(12) United States Patent  
Cobb

(10) Patent No.: US 9,005,932 B2
(45) Date of Patent: Apr. 14, 2015

(54) MUTATIONAL ANALYSIS

(75) Inventor: Ben Cobb, Wiltshire (GB)

(73) Assignee: Epistem Limited, Manchester (GB)

( * ) Notice: Subject to any disclaimer, the term of this patent is extended or adjusted under 35 U.S.C. 154(b) by 253 days.

(21) Appl. No.: 13/345,127

(22) Filed: Jan. 6, 2012

(65) Prior Publication Data

US 2012/0214158 A1 Aug. 23, 2012

(30) Foreign Application Priority Data

Jan. 6, 2011 (GB) .................... 1100150.0

(51) Int. Cl.
C12P 19/34 (2006.01)
C12Q 1/68 (2006.01)

(52) U.S. Cl.
CPC ........ C12Q 1/6858 (2013.01); *C12Q 2527/107* (2013.01); *C12Q 2537/163* (2013.01); *C12Q 2549/119* (2013.01)

(58) Field of Classification Search
USPC ........................................ 435/6.1, 6.12, 91.2
See application file for complete search history.

(56) References Cited

U.S. PATENT DOCUMENTS

| 5,824,476 A | 10/1998 | Wallace |
| 5,849,497 A | 12/1998 | Steinman |
| 7,553,625 B2 * | 6/2009 | Hoon et al. ................. 435/6.16 |
| 2004/0091905 A1 | 5/2004 | Guo |
| 2010/0261186 A1 | 10/2010 | Tanabe |

FOREIGN PATENT DOCUMENTS

| GB | 2293238 | 3/1996 |
| WO | WO-2007106534 | 9/2007 |
| WO | WO-2010111682 | 9/2010 |

OTHER PUBLICATIONS

UK Search Report from GB1100150.0 dated Jul. 22, 2011.
Lee, S. et al., Mutant enrichment with 3" modified oligonucleotides: a practical PCR method for detecting trace mutant DNAs, Journal of Molecular Diagnostics, 13(6): 657-668 (2011).

* cited by examiner

*Primary Examiner* — Ardin Marschel
(74) *Attorney, Agent, or Firm* — Choate, Hall & Stewart LLP; Brenda Herschbach Jarrell

(57) ABSTRACT

A method for analysing genetic mutations, and in particular single nucleotide polymorphisms (SNPs) and/or somatic mutations, is described, as well as methods for preferentially amplifying one allelic form compared with another form. The methods use an oligonucleotide probe which hybridises to a first allele with a lower melting temperature (Tm) than that with which it hybridises to a second allele, together with amplification primers which flank the oligonucleotide probe binding site and which bind to the sample with a higher Tm than that of the probe and the first allele. An amplification reaction may be carried out at a temperature such that the probe is preferentially hybridised to the second allele, thereby amplifying the first allele. The amplified sequences may be detected using the same probe as acted as the blocking probe during amplification.

21 Claims, 26 Drawing Sheets

ATGACTGAATATAAACTTGTGGTAGTTGGAGCTGGTGGC
GTAGGCAAGAGTGCCTTGACGATACAGCTAATTCAGAAT
CATTTTGTGGACGAATATGATCCAACAATAGAGGATTCC
TACAGGAAGCAAGTAGTAATTGATGGAGAAACCTGTCTC
TTGGATATTCTCGACACAGCAGGTCAAGAGGAGTACAG
TGCAATGAGGGACCAGTACATGAGGACTGGGGAGGCT
TTCTTTGTGTATTTGCCATAAATAATACTAAATCATTTGAA
GATATTCACCATTATAGAGAACAAATTAAAGAGTTAAGG
ACTCTGAAGATGTACCTATGGTCCTAGTAGGAAATAAAT
GTGATTTGCCTTCTAGAACAGTAGACACAAAACAGGCTC
AGGACTTAGCAAGAAGTTATGGAATTCCTTTTATTGAAA
CATCAGCAAAGACAAGACAGGGTGTTGATGCCTTC
TATACATTAGTTCGAGAAATTCGAAAACATAAAGAAAAGA
TGAGCAAAGATGGTAAAAGAAGAAAAAGAAGTCAAAGA
CAAAGTGTGTAATTATGTAA

Fig. 1

Codon 61

```
                            F        F
                            ↓        ↓
HYB_KRAS_CD61    5' AGGTCA[C]AGAGGAG AACAGG G 3'
                    |||||||||||||||||||||||
WT_KRAS_CD61     3' TCCAGTTCTCCTCATGTCAC 5'

WT_KRAS_CD61     3' TCCAGA A TCTCCTCATGTCAC 5'
                          ‾
KRAS_Gln61Leu
```

Codon 146

```
                            F        F
                            ↓        ↓
HYB_KRAS_CD146   5' TGTAGT[C]G TTCTGT TCTGT 3'
                    |||||||||||||||||||||||
WT_KRAS_CD146    3' ACATCAG CAAGACAAGACA 5'

WT_KRAS_CD146    3' ACATCAG CAAGACAAGACA 5'

KRAS_Ala146Thr   3' ACATCA A CAAGACAAGACA 5'
```

Fig. 3

| | Genotype | Tm | Difference | Difference C12 - C13 | Duplicate calls ± 0.5°C | ± 0.35°C | ± 0.1°C |
|---|---|---|---|---|---|---|---|
| 1 | Wild type | 62.6°C | | | | | |
| 2 | Gly12Ser | 58.7°C | -6.1°C | 0.1°C | 8, 10 | 8, 10 | 8 |
| 3 | Gly12Arg | 55.7°C | -7.1°C | 0.4°C | 4, 9 | | |
| 4 | Gly12Cys | 56.0°C | -6.6°C | -0.3°C | 3, 10 | | |
| 5 | Gly12Asp | 58.5°C | -4.3°C | 1.1°C | | | |
| 6 | Gly12Ala | 58.3°C | -4.5°C | -1.1°C | 6 | 6 | |
| 7 | Gly12Val | 57.6°C | -5.2°C | -1.6°C | | | |
| 8 | Gly13Ser | 56.5°C | -6.9°C | | 11 | 11 | |
| 9 | Gly13Arg | 55.5°C | -7.0°C | | | | |
| 10 | Gly13Cys | 56.3°C | -6.6°C | | | | |
| 11 | Gly13Asp | 57.4°C | -5.4°C | | | | |
| 12 | Gly13Ala | 58.4°C | -4.5°C | | | | |
| 13 | Gly13Val | 59.5°C | -3.3°C | | | | |

Fig. 5

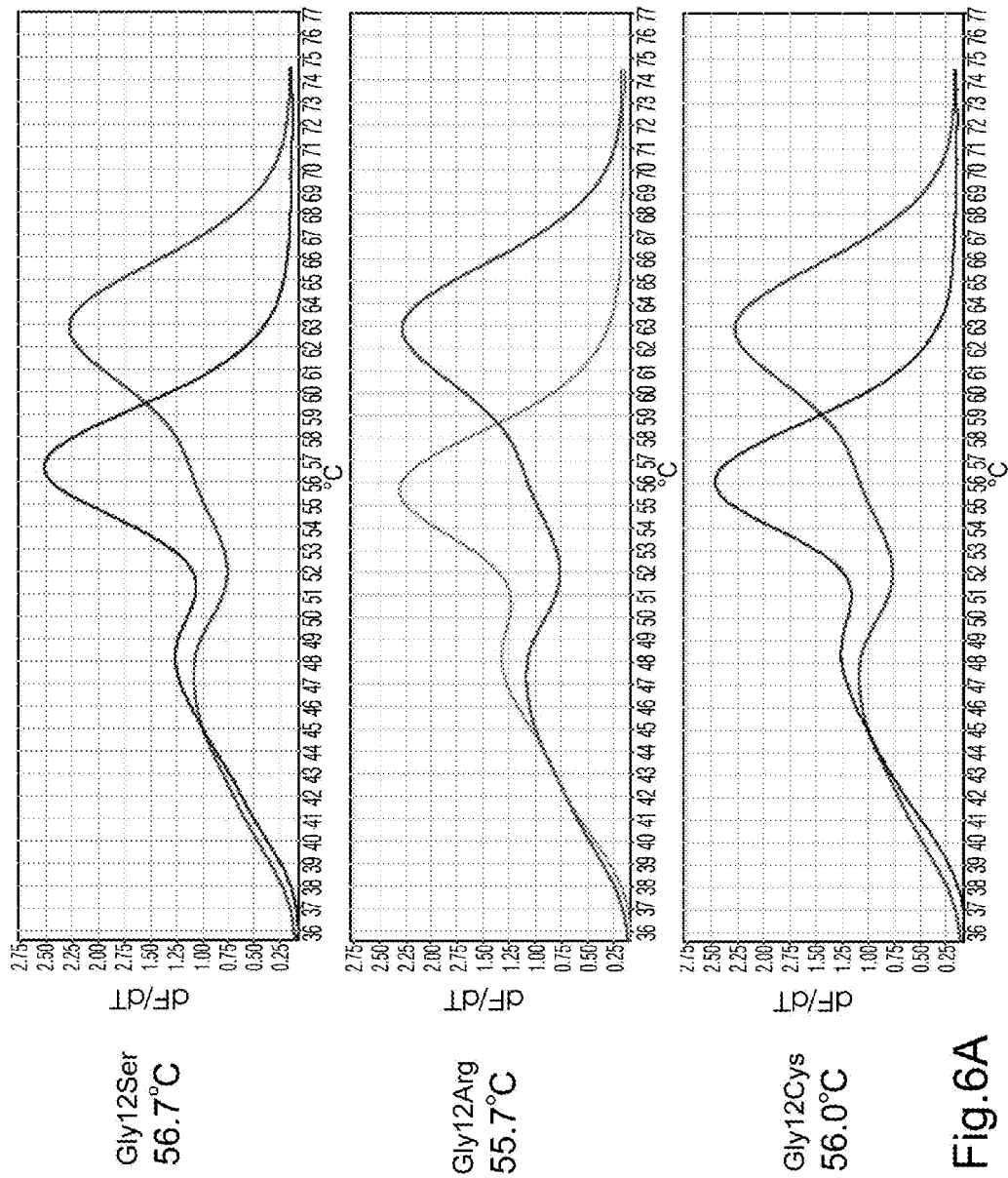

EGFR EXON19 ASSAY

Probe EGFR_EX19_HYB is designed to detect a number of deletions that occur within Exon 19 of the EGFR gene. Deletions will create loop-outs within the hyBeacon probe and reduce the Tm of the probe amplicon duplex.

Synthetic templates shown are to be used to model the effect of sequence variants on probe Tm.

Probe Design

EGFRX19HYB_DEL

WT

```
        F       F
        |       |
CCCGCCGGTACAAGGAATTAAGAGAAGCAACATCTCCGAAAGCC
||||||||||||||||||||||||||||||||||||||||||||
GGGCGGCCGATAGTTCCTTAATTCTCTTCGTTGTAGAGGCTTTCGG
```

Fig. 11

EGFR Exon 19

BRAF V600*

```
AGAAAAGCATGCTCACCTCAACCCTAACCATTCAAGCCCCCAAAAATCTTAAAAGCAGGTTATAAAGCCT
AATACAACTACATGATTGTTTAGACAATCATGATACTAATATTACTACATTCACTGTTAAAGACATGCTTTTTA
AGAATATTAATTATACAGAATTATACAAATTAGAATTAGAACATCATAACATTCATAAACACTTCATAATGCTCTGA
AGGAAAATCACATCACTGTGTTTCCTTACTTACTACAGCTCAGTATATTTCTTCATGAAGACCTCACA
AGTAAAAATAGCTGCATTTCGGATTTTGTGTCGGATGXXXXXXXXXAGTGGGTGCCAATCAGTTTGAAC
GTCTCTGATCCATTTGTTGTCGATGCTAACAATTCAGGCTATTTGCACTGATAAATTTTCGCCC
GAGATGCCCTGAGTTACTAGGAAAGTC

Name    <>  Sequence                                              Comment

NTPROBE  >   5'CTACAGTGAAANCTCGANGG3'                              HyBeacon probe p.600WT  V   3'AGATCGATCGATGTCCTTTAGAGCTACCTCACC5'                 Wild Type
p.V600E  V   3'AGATCGATCGATGTCCCTTTAGAGCTACCTCACC5'                1799 T>A
p.V600G  V   3'AGATCGATCGATGTCCCTTTAGAGCTACCTCACC5'                1799 T>G
p.V600A  V   3'AGATCGATCGATGTCCCTTTAGAGCTACCTCACC5'                1799 T>C
p.V600D  V   3'AGATCGATCGATGTCTATTAGAGCTACCTCACC5'                 1799_1800 TG>AT
p.V600K  V   3'AGATCGATCGATGTTCCTTTAGAGCTACCTCACC5'                1798_1799 GT>AA
p.V600R  V   3'AGATCGATCGATGTTCCTTTAGAGCTACCTCACC5'                1798_1799 GT>AA
p.V600R* V   3'AGATCGATCGATGCTCCTTTAGAGCTACCTCACC5'                1797_1799 AGT>GAG
```

NB: Orientation of mutation templates

Fig. 17

CTTTACTTACTACACCTCAGATATATTTCTTCATGAA
GACCTCACAGTAAAAATAGGTGATTTTGGTCTAGCT
ACAGTGAAATCTCGATGGGTGGGTCCCATCAGTTT
GAACAGTTGTCTGGGATCCATTTGTGGATGGTAAGA
ATTGAG

*Primers underlined; probe target in bold.

Fig. 18

SEQUENCE LISTING

```
<160> NUMBER OF SEQ ID NOS: 59

<210> SEQ ID NO 1
<211> LENGTH: 20
<212> TYPE: DNA
<213> ORGANISM: Artificial Sequence
<220> FEATURE:
<223> OTHER INFORMATION: Probe

<400> SEQUENCE: 1
agttggagct ggtggcgtag                                          20

<210> SEQ ID NO 2
<211> LENGTH: 20
<212> TYPE: DNA
<213> ORGANISM: Artificial Sequence
<220> FEATURE:
<223> OTHER INFORMATION: Probe

<400> SEQUENCE: 2
aggtcaagag gagtacagtg                                          20

<210> SEQ ID NO 3
<211> LENGTH: 20
<212> TYPE: DNA
<213> ORGANISM: Artificial Sequence
<220> FEATURE:
<223> OTHER INFORMATION: Probe

<400> SEQUENCE: 3
tgtagtcgtt tctgttctgt                                          20

<210> SEQ ID NO 4
<211> LENGTH: 20
<212> TYPE: DNA
<213> ORGANISM: Artificial Sequence
<220> FEATURE:
<223> OTHER INFORMATION: Probe

<400> SEQUENCE: 4
gctgggctcc ggtgcgttcg                                          20

<210> SEQ ID NO 5
<211> LENGTH: 45
<212> TYPE: DNA
<213> ORGANISM: Artificial Sequence
<220> FEATURE:
<223> OTHER INFORMATION: Probe

<400> SEQUENCE: 5
cccgtcgcta tcaaggaatt aagagaagca acatctccga aagcc              45

<210> SEQ ID NO 6
<211> LENGTH: 39
<212> TYPE: DNA
<213> ORGANISM: Artificial Sequence
```

```
<220> FEATURE:
<223> OTHER INFORMATION: Probe

<400> SEQUENCE: 6
ctaccggtcg cacggtcgca ccctgttggg ggtgcacac                                39

<210> SEQ ID NO 7
<211> LENGTH: 25
<212> TYPE: DNA
<213> ORGANISM: Artificial Sequence
<220> FEATURE:
<223> OTHER INFORMATION: Probe

<400> SEQUENCE: 7
tgggctggcc aaactgctgg gtgcg                                               25

<210> SEQ ID NO 8
<211> LENGTH: 20
<212> TYPE: DNA
<213> ORGANISM: Artificial Sequence
<220> FEATURE:
<223> OTHER INFORMATION: Probe

<400> SEQUENCE: 8
ctacagtgaa atctcgatgg                                                     20

<210> SEQ ID NO 9
<211> LENGTH: 567
<212> TYPE: DNA
<213> ORGANISM: Artificial Sequence
<220> FEATURE:
<223> OTHER INFORMATION: A partial sequence of wild type K-RAS gene

<400> SEQUENCE: 9
atgactgaat ataaacttgt ggtagttgga gctggtggcg taggcaagag tgccttgacg         60
atacagctaa ttcagaatca ttttgtggac gaatatgatc caacaataga ggattcctac        120
aggaagcaag tagtaattga tggagaaacc tgtctcttgg atattctcga cacagcaggt        180
caagaggagt acagtgcaat gagggaccag tacatgagga ctggggaggg ctttctttgt        240
gtatttgcca taaataatac taaatcattt gaagatattc accattatag agaacaaatt        300
aaaagagtta aggactctga agatgtacct atggtcctag taggaaataa atgtgatttg        360
ccttctagaa cagtagacac aaaacaggct caggacttag caagaagtta tggaattcct        420
tttattgaaa catcagcaaa gacaagacag ggtgttgatg atgccttcta tacattagtt        480
cgagaaattc gaaaacataa agaaaagatg agcaaagatg gtaaaaagaa gaaaagaaag        540
tcaaagacaa agtgtgtaat tatgtaa                                            567

<210> SEQ ID NO 10
<211> LENGTH: 20
<212> TYPE: DNA
<213> ORGANISM: Artificial Sequence
<220> FEATURE:
<223> OTHER INFORMATION: Partial K-RAS wild type sequence

<400> SEQUENCE: 10
tcaacctcga ccaccgcatc                                                    20

<210> SEQ ID NO 11
<211> LENGTH: 20
<212> TYPE: DNA
<213> ORGANISM: Artificial Sequence
<220> FEATURE:
```

<223> OTHER INFORMATION: Mutant K-RAS sequence

<400> SEQUENCE: 11
tcaacctcga tcaccgcatc                                               20

<210> SEQ ID NO 12
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 12
tcaacctcga gcaccgcatc                                               20

<210> SEQ ID NO 13
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 13
tcaacctcga acaccgcatc                                               20

<210> SEQ ID NO 14
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 14
tcaacctcga ctaccgcatc                                               20

<210> SEQ ID NO 15
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 15
tcaacctcga cgaccgcatc                                               20

<210> SEQ ID NO 16
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 16
tcaacctcga caaccgcatc                                               20

<210> SEQ ID NO 17
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 17
tcaacctcga ccatcgcatc                                               20

```
<210> SEQ ID NO 18
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 18
tcaacctcga ccagcgcatc                                          20

<210> SEQ ID NO 19
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 19
tcaacctcga ccaacgcatc                                          20

<210> SEQ ID NO 20
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 20
tcaacctcga ccactgcatc                                          20

<210> SEQ ID NO 21
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 21
tcaacctcga ccacggcatc                                          20

<210> SEQ ID NO 22
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 22
tcaacctcga ccacagcatc                                          20

<210> SEQ ID NO 23
<211> LENGTH: 20
<212> TYPE: DNA
<213> ORGANISM: Artificial Sequence
<220> FEATURE:
<223> OTHER INFORMATION: Partial sequence from wild type K-RAS

<400> SEQUENCE: 23
tccagttctc ctcatgtcac                                          20

<210> SEQ ID NO 24
<211> LENGTH: 20
<212> TYPE: DNA
<213> ORGANISM: Artificial Sequence
<220> FEATURE:
<223> OTHER INFORMATION: Mutant K-RAS sequence
```

```
<400> SEQUENCE: 24
tccagatctc ctcatgtcac                                              20

<210> SEQ ID NO 25
<211> LENGTH: 20
<212> TYPE: DNA
<213> ORGANISM: Artificial Sequence
<220> FEATURE:
<223> OTHER INFORMATION: Partial sequence from wild type K-RAS

<400> SEQUENCE: 25
acatcagcaa agacaagaca                                              20

<210> SEQ ID NO 26
<211> LENGTH: 20
<212> TYPE: DNA
<213> ORGANISM: Artificial Sequence
<220> FEATURE:
<223> OTHER INFORMATION: Mutant K-RAS sequence

<400> SEQUENCE: 26
acatcaacaa agacaagaca                                              20

<210> SEQ ID NO 27
<211> LENGTH: 20
<212> TYPE: DNA
<213> ORGANISM: Artificial Sequence
<220> FEATURE:
<223> OTHER INFORMATION: Partial sequence from wild type EGFR

<400> SEQUENCE: 27
cgacccgagg ccacgcaagc                                              20

<210> SEQ ID NO 28
<211> LENGTH: 20
<212> TYPE: DNA
<213> ORGANISM: Artificial Sequence
<220> FEATURE:
<223> OTHER INFORMATION: Mutant EGFR sequence

<400> SEQUENCE: 28
cgactcgagg ccacgcaagc                                              20

<210> SEQ ID NO 29
<211> LENGTH: 20
<212> TYPE: DNA
<213> ORGANISM: Artificial Sequence
<220> FEATURE:
<223> OTHER INFORMATION: Mutant EGFR sequence

<400> SEQUENCE: 29
cgacacgagg ccacgcaagc                                              20

<210> SEQ ID NO 30
<211> LENGTH: 20
<212> TYPE: DNA
<213> ORGANISM: Artificial Sequence
<220> FEATURE:
<223> OTHER INFORMATION: Mutant EGFR sequence

<400> SEQUENCE: 30
cgaccggagg ccacgcaagc                                              20

<210> SEQ ID NO 31
<211> LENGTH: 45
```

```
<212> TYPE: DNA
<213> ORGANISM: Artificial Sequence
<220> FEATURE:
<223> OTHER INFORMATION: Partial sequence from wild type EGFR

<400> SEQUENCE: 31
gggcagcgat agttccttaa ttctcttcgt tgtagaggct ttcgg             45

<210> SEQ ID NO 32
<211> LENGTH: 30
<212> TYPE: DNA
<213> ORGANISM: Artificial Sequence
<220> FEATURE:
<223> OTHER INFORMATION: Mutant EGFR sequence

<400> SEQUENCE: 32
gggcagcgat agttttgtag aggctttcgg                              30

<210> SEQ ID NO 33
<211> LENGTH: 27
<212> TYPE: DNA
<213> ORGANISM: Artificial Sequence
<220> FEATURE:
<223> OTHER INFORMATION: Mutant EGFR sequence

<400> SEQUENCE: 33
gggcagcgat agttcagagg ctttcgg                                 27

<210> SEQ ID NO 34
<211> LENGTH: 30
<212> TYPE: DNA
<213> ORGANISM: Artificial Sequence
<220> FEATURE:
<223> OTHER INFORMATION: Mutant EGFR sequence

<400> SEQUENCE: 34
gggcagcgat agttccgtag aggctttcgg                              30

<210> SEQ ID NO 35
<211> LENGTH: 27
<212> TYPE: DNA
<213> ORGANISM: Artificial Sequence
<220> FEATURE:
<223> OTHER INFORMATION: Mutant EGFR sequence

<400> SEQUENCE: 35
gggcagcgat agttccgagg ctttcgg                                 27

<210> SEQ ID NO 36
<211> LENGTH: 36
<212> TYPE: DNA
<213> ORGANISM: Artificial Sequence
<220> FEATURE:
<223> OTHER INFORMATION: Mutant EGFR sequence

<400> SEQUENCE: 36
gggcagcgat agttccttcg ttgtagaggc tttcgg                       36

<210> SEQ ID NO 37
<211> LENGTH: 30
<212> TYPE: DNA
<213> ORGANISM: Artificial Sequence
<220> FEATURE:
<223> OTHER INFORMATION: Mutant EGFR sequence

<400> SEQUENCE: 37
```
gggcagcgat agttccttag aggctttcgg        30

<210> SEQ ID NO 38
<211> LENGTH: 27
<212> TYPE: DNA
<213> ORGANISM: Artificial Sequence
<220> FEATURE:
<223> OTHER INFORMATION: Mutant EGFR sequence

<400> SEQUENCE: 38
gggcagcgat agttccttgg cttcgg        27

<210> SEQ ID NO 39
<211> LENGTH: 33
<212> TYPE: DNA
<213> ORGANISM: Artificial Sequence
<220> FEATURE:
<223> OTHER INFORMATION: Mutant EGFR sequence

<400> SEQUENCE: 39
gggcagcgat agttccttag tagaggcttt cgg        33

<210> SEQ ID NO 40
<211> LENGTH: 30
<212> TYPE: DNA
<213> ORGANISM: Artificial Sequence
<220> FEATURE:
<223> OTHER INFORMATION: Mutant EGFR sequence

<400> SEQUENCE: 40
gggcagcgat agttccttag aggctttcgg        30

<210> SEQ ID NO 41
<211> LENGTH: 27
<212> TYPE: DNA
<213> ORGANISM: Artificial Sequence
<220> FEATURE:
<223> OTHER INFORMATION: Mutant EGFR sequence

<400> SEQUENCE: 41
gggcagcgat agttccttag ctttcgg        27

<210> SEQ ID NO 42
<211> LENGTH: 30
<212> TYPE: DNA
<213> ORGANISM: Artificial Sequence
<220> FEATURE:
<223> OTHER INFORMATION: Partial sequence of wild type EGFR

<400> SEQUENCE: 42
gatggccagc gtggacaacc cccacgtgtg        30

<210> SEQ ID NO 43
<211> LENGTH: 30
<212> TYPE: DNA
<213> ORGANISM: Artificial Sequence
<220> FEATURE:
<223> OTHER INFORMATION: Mutant EGFR sequence

<400> SEQUENCE: 43
gatggccatc gtggacaacc cccacgtgtg        30

<210> SEQ ID NO 44
<211> LENGTH: 39
<212> TYPE: DNA
<213> ORGANISM: Artificial Sequence

```
<220> FEATURE:
<223> OTHER INFORMATION: Mutant EGFR sequence

<400> SEQUENCE: 44
gatggccagc gtgccagcgt gggacaaccc ccacgtgtg                    39

<210> SEQ ID NO 45
<211> LENGTH: 33
<212> TYPE: DNA
<213> ORGANISM: Artificial Sequence
<220> FEATURE:
<223> OTHER INFORMATION: Mutant EGFR sequence

<400> SEQUENCE: 45
gatggccagc gtggacaacc cccaccacgt gtg                          33

<210> SEQ ID NO 46
<211> LENGTH: 33
<212> TYPE: DNA
<213> ORGANISM: Artificial Sequence
<220> FEATURE:
<223> OTHER INFORMATION: Mutant EGFR sequence

<400> SEQUENCE: 46
gatggccagc gtggacggta accccacgt gtg                           33

<210> SEQ ID NO 47
<211> LENGTH: 25
<212> TYPE: DNA
<213> ORGANISM: Artificial Sequence
<220> FEATURE:
<223> OTHER INFORMATION: Partial sequence of wild type EGFR

<400> SEQUENCE: 47
acccgaccgg tttgacgacc cacgc                                   25

<210> SEQ ID NO 48
<211> LENGTH: 25
<212> TYPE: DNA
<213> ORGANISM: Artificial Sequence
<220> FEATURE:
<223> OTHER INFORMATION: Mutant EGFR sequence

<400> SEQUENCE: 48
acccgcccgg tttgacgacc cacgc                                   25

<210> SEQ ID NO 49
<211> LENGTH: 25
<212> TYPE: DNA
<213> ORGANISM: Artificial Sequence
<220> FEATURE:
<223> OTHER INFORMATION: Mutant EGFR sequence

<400> SEQUENCE: 49
acccgaccgg tttgtcgacc cacgc                                   25

<210> SEQ ID NO 50
<211> LENGTH: 436
<212> TYPE: DNA
<213> ORGANISM: Artificial Sequence
<220> FEATURE:
<223> OTHER INFORMATION: Partial sequence of BRAF gene

<400> SEQUENCE: 50
ggaaagcatc tcacctcatc ctaacacatt tcaagcccca aaatcttaa aagcaggtta    60
```

```
tataggctaa tagaactaat cattgtttta gacatactta ttgactctaa gaggaaagat    120
gaagtactat gttttaagaa tattatatta cagaattata gaaattagat ctcttaccct    180
aaactcttca taatgcttgc tctgaaggaa aatgagatct actgttttcc tttacttact    240
acacctcaga tatatttctt catgaagacc tcaagtaaaa ataggtgatt ttggtctagc    300
tacagtgaaa tctcgatgga gtgggtccca tcagtttgaa cgttgtctgg atccatttg    360 tggatggtaa gaattgaggc tattttttcca ctgattaaat ttttggcccg agatgctgct    420
gagttactag aaagtc                                                    436

<210> SEQ ID NO 51
<211> LENGTH: 30
<212> TYPE: DNA
<213> ORGANISM: Artificial Sequence
<220> FEATURE:
<223> OTHER INFORMATION: Partial sequence from wild type BRAF gene

<400> SEQUENCE: 51
agatcgatgt cactttagag ctacctcacc                                      30

<210> SEQ ID NO 52
<211> LENGTH: 30
<212> TYPE: DNA
<213> ORGANISM: Artificial Sequence
<220> FEATURE:
<223> OTHER INFORMATION: Mutant BRAF sequence

<400> SEQUENCE: 52
agatcgatgt ctctttagag ctacctcacc                                      30

<210> SEQ ID NO 53
<211> LENGTH: 30
<212> TYPE: DNA
<213> ORGANISM: Artificial Sequence
<220> FEATURE:
<223> OTHER INFORMATION: Mutant BRAF sequence

<400> SEQUENCE: 53
agatcgatgt cccttagag ctacctcacc                                       30

<210> SEQ ID NO 54
<211> LENGTH: 30
<212> TYPE: DNA
<213> ORGANISM: Artificial Sequence
<220> FEATURE:
<223> OTHER INFORMATION: Mutant BRAF sequence

<400> SEQUENCE: 54
agatcgatgt cgctttagag ctacctcacc                                      30

<210> SEQ ID NO 55
<211> LENGTH: 30
<212> TYPE: DNA
<213> ORGANISM: Artificial Sequence
<220> FEATURE:
<223> OTHER INFORMATION: Mutant BRAF sequence

<400> SEQUENCE: 55
agatcgatgt ctatttagag ctacctcacc                                      30

<210> SEQ ID NO 56
<211> LENGTH: 30
<212> TYPE: DNA
<213> ORGANISM: Artificial Sequence
```

```
<220> FEATURE:
<223> OTHER INFORMATION: Mutant BRAF sequence

<400> SEQUENCE: 56
agatcgatgt ttctttagag ctacctcacc                                         30

<210> SEQ ID NO 57
<211> LENGTH: 30
<212> TYPE: DNA
<213> ORGANISM: Artificial Sequence
<220> FEATURE:
<223> OTHER INFORMATION: Mutant BRAF sequence

<400> SEQUENCE: 57
agatcgatgt tcctttagag ctacctcacc                                         30

<210> SEQ ID NO 58
<211> LENGTH: 30
<212> TYPE: DNA
<213> ORGANISM: Artificial Sequence
<220> FEATURE:
<223> OTHER INFORMATION: Mutant BRAF sequence

<400> SEQUENCE: 58
agatcgatgc tcctttagag ctacctcacc                                         30

<210> SEQ ID NO 59
<211> LENGTH: 150
<212> TYPE: DNA
<213> ORGANISM: Artificial Sequence
<220> FEATURE:
<223> OTHER INFORMATION: Partial sequence from wild type BRAF gene

<400> SEQUENCE: 59
ctttacttac tacacctcag atatatttct tcatgaagac ctcacagtaa aaataggtga        60
ttttggtcta gctacagtga aatctcgatg ggtgggtccc atcagtttga acagttgtct      120
ggatccattt tgtggatggt aagaattgag                                       150
```

MUTATIONAL ANALYSIS

CROSS-REFERENCE TO RELATED APPLICATIONS

The present application claims priority to Great Britain Application No. 1100150.0, filed Jan. 6, 2011, the entire contents of which is incorporated herein by reference.

FIELD OF THE INVENTION

The present invention relates to a method for analysing genetic mutations, and in particular single nucleotide polymorphisms (SNPs) and/or somatic mutations. Aspects of the invention also relate to methods for preferentially amplifying one allelic form compared with another form. Still further aspects of the invention relate to nucleic acid probes of use in analysing genetic mutations.

BACKGROUND

Single nucleotide polymorphisms (SNPs) are believed to be of significant potential importance for personalised medicine; it is possible that certain SNPs which result in single amino acid changes may give rise to variation in patient responsiveness to certain treatment regimes. SNPs may also be of importance in the development of cancers and other cell proliferative disorders, again with mutations in somatic cells activating certain oncogenes.

It is important to be able to determine which SNPs are present in a patient. The melting temperature (Tm) of double stranded DNA depends on the extent of base pair hybridisation; where there is a mismatch between a probe and a target sequence (for example, due to the presence of a SNP) then the Tm will differ compared with when there is no mismatch. Methods involving detecting changes in melting temperature (Tm) of DNA hybridisation between a specific oligonucleotide probe and a gene target when a SNP is present are known. However, somatic cell mutations suffer from the problem that the mutant sequence is likely to be present only in a very few copies in a particular sample, with the wild type sequence predominating. It would be useful to be able to selectively amplify the mutant sequence, for example by polymerase chain reaction (PCR) type techniques.

U.S. Pat. No. 5,849,497 describes specific inhibition of PCR amplification using an oligonucleotide blocking probe which hybridises to a region of interest, but which also includes 3' mismatched bases, which do not hybridise. This mismatch prevents strand extension during PCR. This method is said to be useful for preventing amplification of a specific known sequence. The patent suggests use of the method of prevent amplification of an allele including an inserted sequence by designing a blocking probe to the inserted region. However, this patent does not teach methods for selectively amplifying one SNP variation compared with another. Further, it is necessary to know the target sequence of interest.

Bender et al, Biotechniques 2007, vol 42 no 5, pp 609-614, describe the use of a PNA (peptide nucleic acid) blocking probe to prevent DNA-mediated PCR product formation in prokaryotic RT-PCR. The probe is designed to bind to a region in the genomic DNA which is not present in cDNA generated from mRNA; thus, only cDNA will be amplified, not genomic DNA.

Vestheim and Jarman, Frontiers in Zoology 2008, 5:12, describe the use of blocking primers to prevent PCR amplification of krill DNA sequences and allow amplification of prey DNA from krill stomach content samples. The primers are designed against krill rDNA sequences.

It is among the objects of the present invention to provide a method whereby a variant SNP sequence can be selectively amplified from a sample containing both the variant and the wild type sequence. It is further among objects of aspects of the invention to provide a method whereby amplified sequences can be analysed for SNP content.

SUMMARY

According to a first aspect of the present invention, there is provided a method of preferentially amplifying and detecting a first allele of a locus having at least first and second alleles, the method comprising:
  a) providing a reaction mix comprising
    i) a sample including nucleic acid representing at least the locus to be amplified;
    ii) an oligonucleotide probe which hybridises to the first allele with a lower melting temperature (Tm) than that with which it hybridises to the second allele;
    iii) a pair of oligonucleotide primers for nucleic acid amplification, the primers hybridising to the nucleic acid in the sample at first and second sites flanking the oligonucleotide probe binding site; wherein the Tm of the primer:sample is higher than the Tm of the probe: first allele;
  b) maintaining the reaction mix at a temperature between the probe:first allele Tm and the probe:second allele Tm, such that the probe preferentially hybridises to the second allele;
  c) carrying out a thermal cycling amplification on the reaction mix, the amplification including a melt phase, an annealing phase, and an extension phase, in which the temperatures of the extension and annealing phases are between the probe:first allele Tm and the probe:second allele Tm, such that the probe is hybridised to the second allele during these phases; to thereby amplify the first allele; and
  d) detecting hybridisation of the probe to the sample at a temperature at or below the probe:first allele Tm; detecting hybridisation of the probe to the sample at a higher temperature at or below the probe:second allele Tm; and comparing the two; to thereby detect the amplified first allele.

Thus, the present invention allows a first allele, for example a mutant allele, to be preferentially amplified compared with a second allele, for example, a wild type allele. Further, the amplified sequences may be detected using the same probe as acted as the blocking probe during amplification. This simplifies the procedure significantly.

The temperatures of the extension and annealing phases may be the same, but are preferably different. The temperature of the melt phase may be higher than the temperatures of the Tm primer:sample and the Tm probe:second allele. However, this is not essential; for example, the Tm primer:sample may be lower than the Tm probe:second allele, in which case the melt phase may be at a temperature between these two values, such that effectively the probe remains hybridised to the second allele throughout the amplification reaction.

During the extension phase, the oligonucleotide probe remains hybridised to the second allele. This prevents strand extension of the primer hybridised to the same nucleic acid, whereas primers hybridised to the first allele are free to undergo strand extension since the probe is not hybridised to that allele. In this way, the first allele will be preferentially amplified. As noted below, in certain embodiments one or both of the primers may overlap with the probe binding site such that the probe competes with the primer for binding; this can prevent binding of the primer and hence strand extension.

In other embodiments the primers and probe do not overlap, but the primer prevents further strand extension.

The locus may be a multi-allelic locus; that is, there are more than two alleles possible at that locus. In such a situation, one allele may be designated the wild type allele, and the others are mutant alleles. The probe is preferably selected such that the Tm probe:wild type allele is lower than any of the Tm probe:mutant allele. The method may be used to preferentially amplify any of the mutant alleles which are present. This is of particular benefit when the method is used to investigate somatic mutations, where there may be several different mutations present in different cell lines. In preferred embodiments, the Tm of each possible probe:allele combination differs. Preferably the Tm differs by at least 0.25 C. degree, more preferably at least 0.5 C. degree, most preferably at least 0.75 C. degree. This allows for fine discrimination to be made between each allele. For example, if there are four alleles, and only two are to be amplified, then the extension temperature may be set at an appropriate level such that the probe hybridises to the other two of the alleles.

The probe is preferably substantially, and more preferably fully, complementary to one strand of the target allele. The probe may be fully complementary to one strand of the second allele. The first allele may differ from the sequence of the second allele by one or more point mutations (single nucleotide polymorphisms, SNPs). It is possible that the first allele includes more than one SNP, for example at different codons. It is one of the advantages of the present method that it is possible to preferentially amplify mutant alleles potentially including more than one SNP. Alternatively, the first allele may differ from the sequence of the second allele by one or more deletions.

Preferably the probe is DNA.

The differences in sequence between the first and second alleles are preferably internal to the region where the probe binds; that is, any mismatches between the probe and the first allele are not at the ends of the probe.

The probe may be up to 10, 20, 30, 40, or 50 nucleotides in length. Longer or shorter probes are possible, although it may be difficult to attain suitable discrimination between Tm for different alleles or with the Tm of the primers with shorter probes.

The probe may be labelled. For example, the probe may include a fluorescent or a radioactive label, or may be labelled with a ligand to which a secondary probe may bind. Preferably the probe is labelled with a fluorescent label, and preferably also the label generates a differential signal depending on whether the probe has hybridised to a target strand (that is, the probe is part of a double stranded nucleic acid) or not (the probe is single stranded). A preferred probe is a HyBeacon® probe (see, for example, Mol Cell Probes. 2002 October; 16(5):319-26, "Ultra-rapid DNA analysis using HyBeacon probes and direct PCR amplification from saliva", French D J, Archard C L, Andersen M T, McDowell D G). Generation of differential signals allows easy and rapid analysis of whether the probe has bound to a target.

The step of detecting hybridised probe molecules may further comprise quantification of the relative amounts of first and second alleles in the amplification mix. In certain embodiments of the invention, a detection step may be carried out before as well as after the amplification step. In a preferred embodiment, the ratio of first to second alleles may be measured by: maintaining the reaction mix at a first temperature at or below the Tm of the probe:first allele; detecting hybridised probe molecules; increasing the reaction mix to a second temperature above the Tm of the probe:first allele but at or below the Tm of the probe:second allele; and detecting hybridised probe molecules. At the first, lower temperature, probe will be hybridised to both first and second alleles, while at the second higher temperature, probe will be hybridised only to the second allele.

Where the locus is multi-allelic, then the detection step may further comprise raising the reaction mix to one or more intermediate temperatures, and detecting hybridised probe molecules at each intermediate temperature. This is particularly preferred when each probe:allele combination has a distinct Tm. This embodiment of the invention allows both amplification and quantification of multiple distinct mutant alleles in a single experiment.

The primers preferably bind at a region outside the region where the probe binds; that is, a first primer binds 3'-wards of the probe target, while a second primer binds 5'-wards of the probe target (bearing in mind that the primers will bind to different strands of the duplex DNA). When the primers undergo strand extension, this is blocked by the bound probe, such that the strand cannot be amplified. In certain embodiments the primers may bind adjacent to the region where the probe binds, or may even overlap with the probe by one, two, three, or more nucleotides, although this is not preferred.

Of course, the two primers may overlap with the probe target to different extents, or one may overlap and the other may not. Where the probe and the primer overlap, then the probe may compete with the primer for binding, preferably at the 3' end of the primer, and prevent extension in this way.

In preferred embodiments of the invention, the amplification reaction is polymerase chain reaction (PCR). In certain embodiments, the primers may be provided in different concentrations; preferably one of the primers is provided in a rate-limiting amount, and the amplification reaction is asymmetric PCR. In asymmetric PCR, one of the two target DNA strands is preferentially amplified, as the rate-limiting primer is used up so only the other primer is available to begin strand extension. Either the sense or the antisense strand may be the one targeted for preferential amplification; preferably the preferentially amplified strand is the complementary strand to the probe.

The target locus may be any suitable locus which is thought to contain polymorphisms, for example SNPs. Preferred target loci are the KRAS, EGFR, or BRAF human genes. In preferred embodiments, the target loci are selected from codons 12 and 13 of KRAS, codon 61 of KRAS, and codon 146 of KRAS. Alternatively, the target loci may be any or all of exons 18, 19, 20, or 21 of EGFR. A further alternative would be amino acid residue 600 of BRAF, and corresponding nucleotide residues.

Preferred probe sequences include:

5' AGTTGGAGCTGGTGGCGTAG 3' (HYB_KRAS_CD12/13, SEQ ID NO 1), targeting codons 12 and 13 of KRAS 5' AGGTCAAGAGGAGTACAGTG 3' (HYB_KRAS_CD61, SEQ ID NO 2), targeting codon 61 of KRAS 5' TGTAGTCGTTTCTGTTCTGT 3' (HYB_KRAS_CD146, SEQ ID NO 3), targeting codon 146 of KRAS 5' GCTGGGCTCCGGTGCGTTCG 3' (EGFRX18_HYB, SEQ ID NO 4), targeting exon 18 of EGFR 5' CCCGTCGCTATCAAGGAATTAAGAGAAGCAACATCTCCGAAAGCC 3' (EGFRX19HYB_DEL, SEQ ID NO 5), targeting exon 19 of EGFR 5' CTACCGGTCGCACGGTCGCACCCTGTTGGGGGT-GCACAC 3' (EGFRX20_HYB, SEQ ID NO 6), targeting exon 20 of EGFR 5' TGGGCTGGCCAAACTGCTGGGTGCG 3' (EGFR-X21_HYB, SEQ ID NO 7), targeting exon 21 of EGFR 5' CTACAGTGAAATCTCGATGG 3' (BRAF_V600, SEQ ID NO 8), targeting amino acid 600 of BRAF.

The present invention also provides an oligonucleotide probe comprising or consisting of a nucleotide sequence selected from SEQ ID NO 1 to SED ID NO 8. The probes are preferably DNA. The probes may further comprise one or more labels associated with the probe; preferably a fluorescent label associated with one or more nucleotides of the sequence. The labels may be selected so as to give a differential signal depending on whether the probe is in a double stranded duplex with a target sequence or is single stranded.

Also provided is a primer sequence selected to allow amplification of a target sequence recognised by the above-mentioned probes SEQ ID NO 1 to SEQ ID NO 8.

A further aspect of the present invention provides a method for detecting somatic mutations in a sample from a subject, the sample comprising nucleic acid from a locus having at least first and second alleles, the first allele being a mutant allele and the second allele being a wild type allele, the method comprising
 a) providing a reaction mix comprising
  i) the sample;
  ii) an oligonucleotide probe which hybridises to the first allele with a lower melting temperature (Tm) than that with which it hybridises to the second allele;
  iii) a pair of oligonucleotide primers for nucleic acid amplification, the primers hybridising to the nucleic acid in the sample at first and second sites flanking the oligonucleotide probe binding site; wherein the Tm of the primer:sample is higher than the Tm of the probe:first allele;
 b) maintaining the reaction mix at a temperature between the probe:first allele Tm and the probe:second allele Tm, such that the probe preferentially hybridises to the second allele;
 c) carrying out a thermal cycling amplification on the reaction mix, the amplification including a melt phase, an annealing phase, and an extension phase, in which the temperatures of the extension and annealing phases are between the probe:first allele Tm and the probe:second allele Tm, such that the probe is hybridised to the second allele during these phases; to thereby amplify the first allele;
 d) maintaining the temperature of the reaction mix at or below the Tm probe:mutant allele;
 e) maintaining the temperature of the reaction mix above the temperature in step d), but at or below the Tm probe:wild type allele; and
 f) detecting hybridised probe in steps d) and e), to thereby determine the presence or absence of the mutant allele in the sample.

BRIEF DESCRIPTION OF THE DRAWING

The drawings are for illustration purposes only, not for limitation.

FIG. 1 depicts a partial nucleic acid sequence of a wild type K-RAS gene (SEQ ID NO. 9). Target regions in codons 12/13, 16 and 167 are highlighted in bold.

FIG. 3 depicts exemplary probes (HYB_KRAS_CD61—SEQ ID NO. 2; HYB_KRAS_CD146—SEQ ID NO. 3), along with wild type (WT_KRAS_CD61—SEQ ID NO. 23; WT_KRAS_CD146—SEQ ID NO. 25) and mutant sequences (KRAS_Gln61Leu—SEQ ID NO. 24; KRASAla146Thr—SEQ ID NO. 26) for the regions around codons 61 and 146 of the K-RAS gene.

FIG. 5 presents data indicating the Tm for the HYB_KRAS_CD12/13 probe hybridized to each of the wild type and mutant K-RAS alleles.

FIG. 6A-D presents data depicting the melt curve for each of the CD 12/13 alleles compared to the wild type melt curve.

FIG. 11 depicts the EGFRX19HYB_DEL exon 19 probe (SEQ ID NO. 5) and wild type nucleic acid sequence (WT—SEQ ID NO 31).

FIG. 12 depicts the EGFRX19HYB_DEL probe (SEQ ID NO. 5) hybridised to wild type (EGFRx19_WT—SEQ ID NO. 31) and deletion mutations (EGFRx19_2235_2249—SEQ ID NO. 32; EGFRx19 2236 2253—SEQ ID NO. 33; EGFRx1922372251—SEQ ID NO. 34; EGFRx19 2237 2254—SEQ ID NO. 35; EGFRx19 2239 2247—SEQ ID NO. 36; EGFRx19 2239 2253—SEQ ID NO. 37; EGFRx19 2239 2256—SEQ ID NO. 38; EGFRx19 2240 2251—SEQ ID NO. 39; EGFRx19 2240 2254—SEQ ID NO. 40; and EGFRx19_2240_2257—SEQ ID NO. 41) within exon 19 of EGFR. The underlined regions of the probe do not hybridise to the target and form a loop.

FIG. 13 depicts the EGFR_EX20_HYB probe (SEQ ID NO. 6), a wild type sequence (EGFRx20WT—SEQ ID NO. 42) and various SNPs with their corresponding nucleic acid substitutions (EGFRx20202303G/T—SEQ ID NO. 43; EGFRx20_2307IN9—SEQ ID NO. 44; EGFRx2023191N3—SEQ ID NO. 45; EGFRx2023101N3—SEQ ID NO. 46) within exon 20 of the EGFR gene.

47) and various SNPs with their corresponding nucleic acid substitutions (EGFRx21__1573_T>G—SEQ ID NO. 48; and EGFRx21__2182_T>A—SEQ ID NO. 49) within exon 21 of the EGFR gene.

Figure 15:
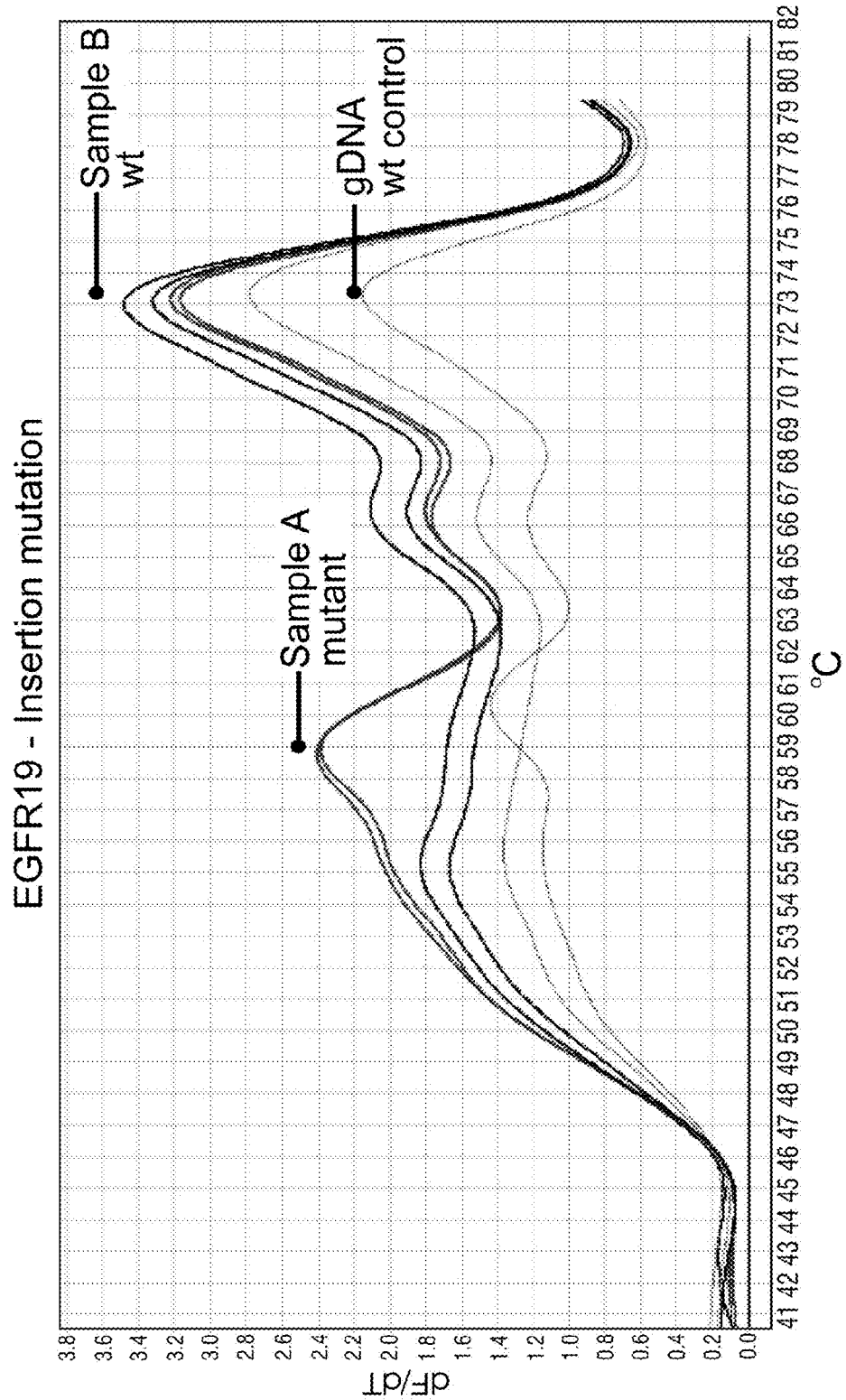

FIG. 15 presents data depicting the melt curve for samples tested with the EGFRX19_HYB probe.

Figure 16:
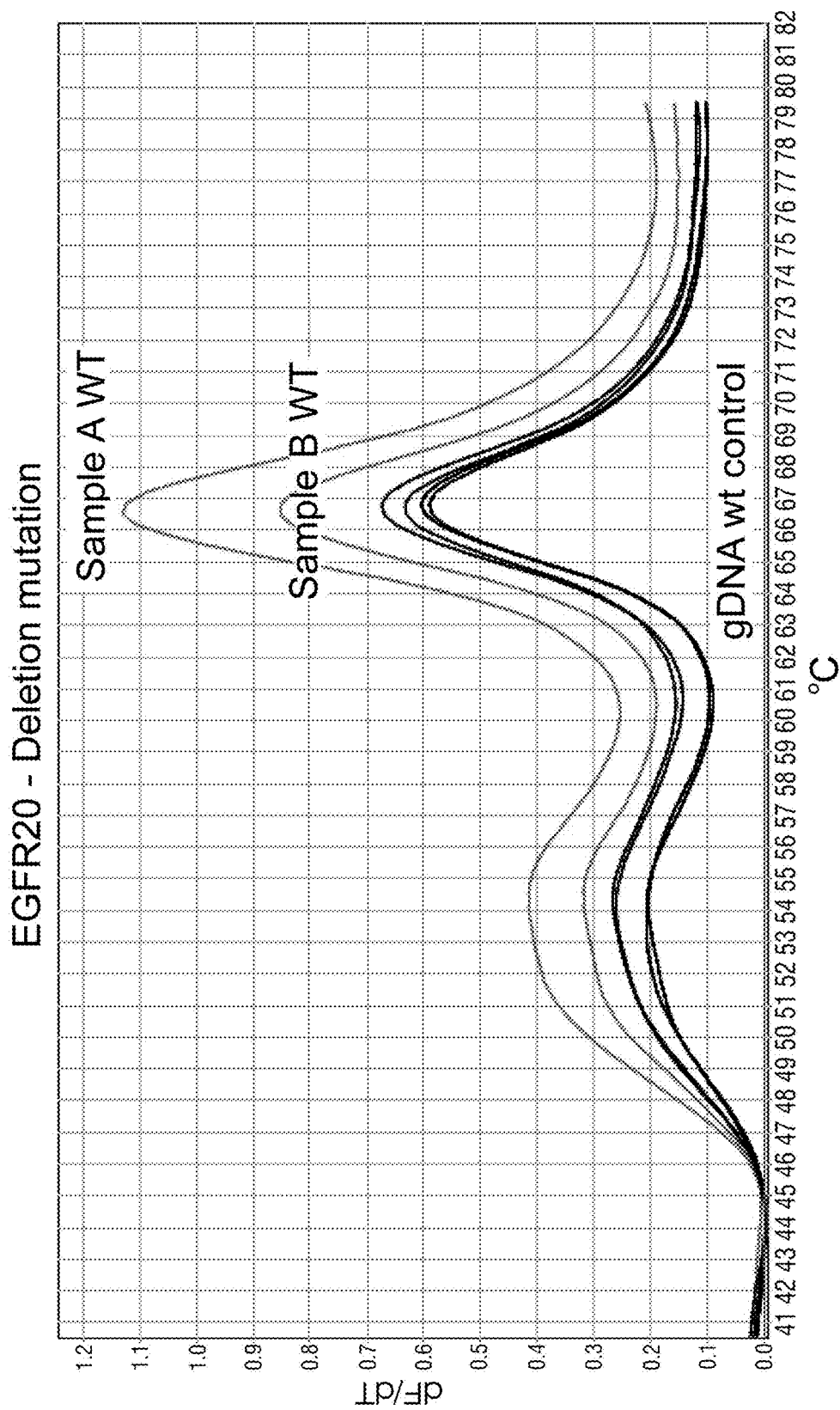

FIG. 16 presents data depicting the melt curve for samples tested with the EGFRX20_HYB probe.

FIG. 17 depicts a partial sequence of the of BRAF gene (SEQ ID NO. 50) encompassing the V600 region. As depicted is the BRAF V600 probe (WTPROBE—SEQ ID NO. 8), a wild type sequence (P.600WT—SEQ ID NO. 51) and various SNPs, along with their corresponding amino acid substitutions (p.V600E—SEQ ID NO. 52; p.V600G—SEQ ID NO. 53; p.V600A—SEQ ID NO. 54; p.V600D—SEQ ID NO. 55; p.V600K—SEQ ID NO. 56; p.V600R—SEQ ID NO. 57; p.V600R*—SEQ ID NO. 58) within the BRAF V600 region.

FIG. 18 depicts a portion of the V600 region of the nucleic acid sequence encoding the BRAF gene (SEQ ID NO. 59). Underlined sequences denote the nucleic acid sequences of each primer used to amplify a BRAFV600 amplicon.

Figure 19:
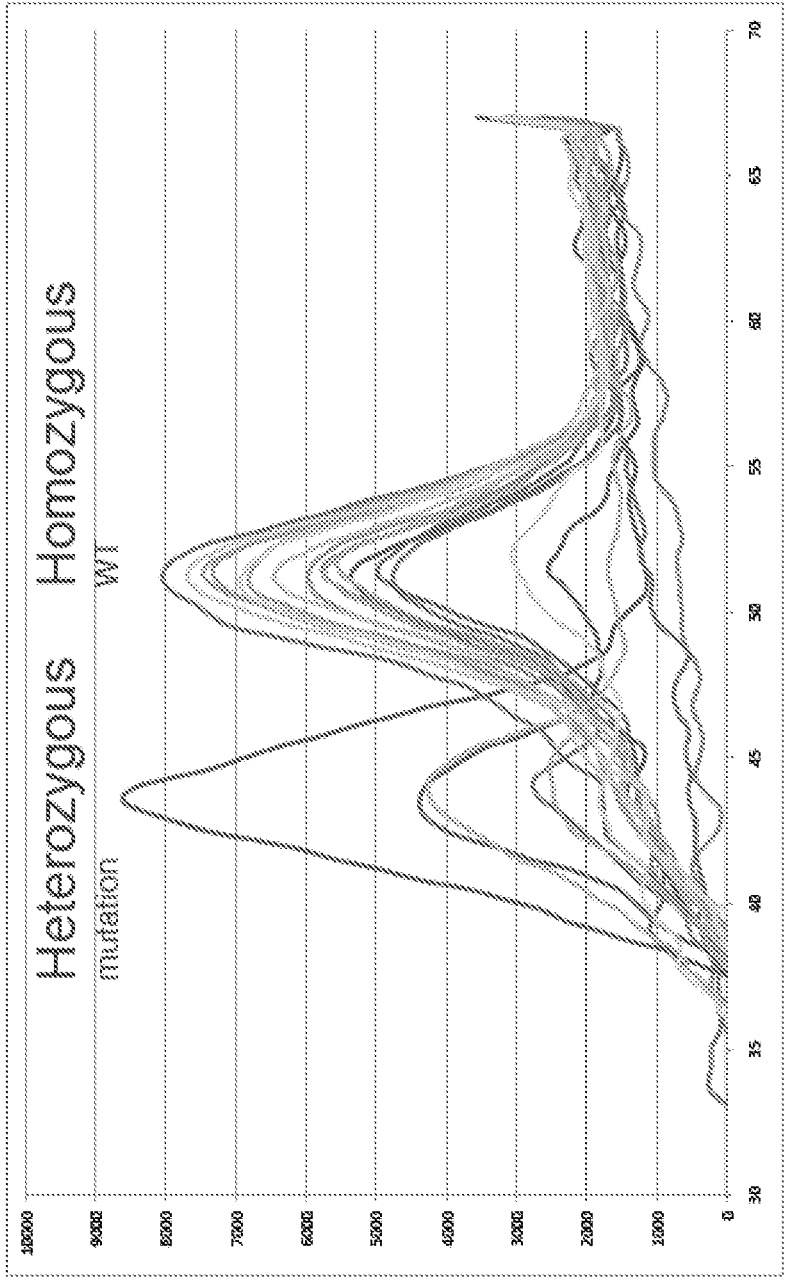

FIG. 19 presents data depicting the melt temp of various samples, following PCR amplification and hybridization analysis of the BRAFV600 region by real-time PCR.

Figure 20:
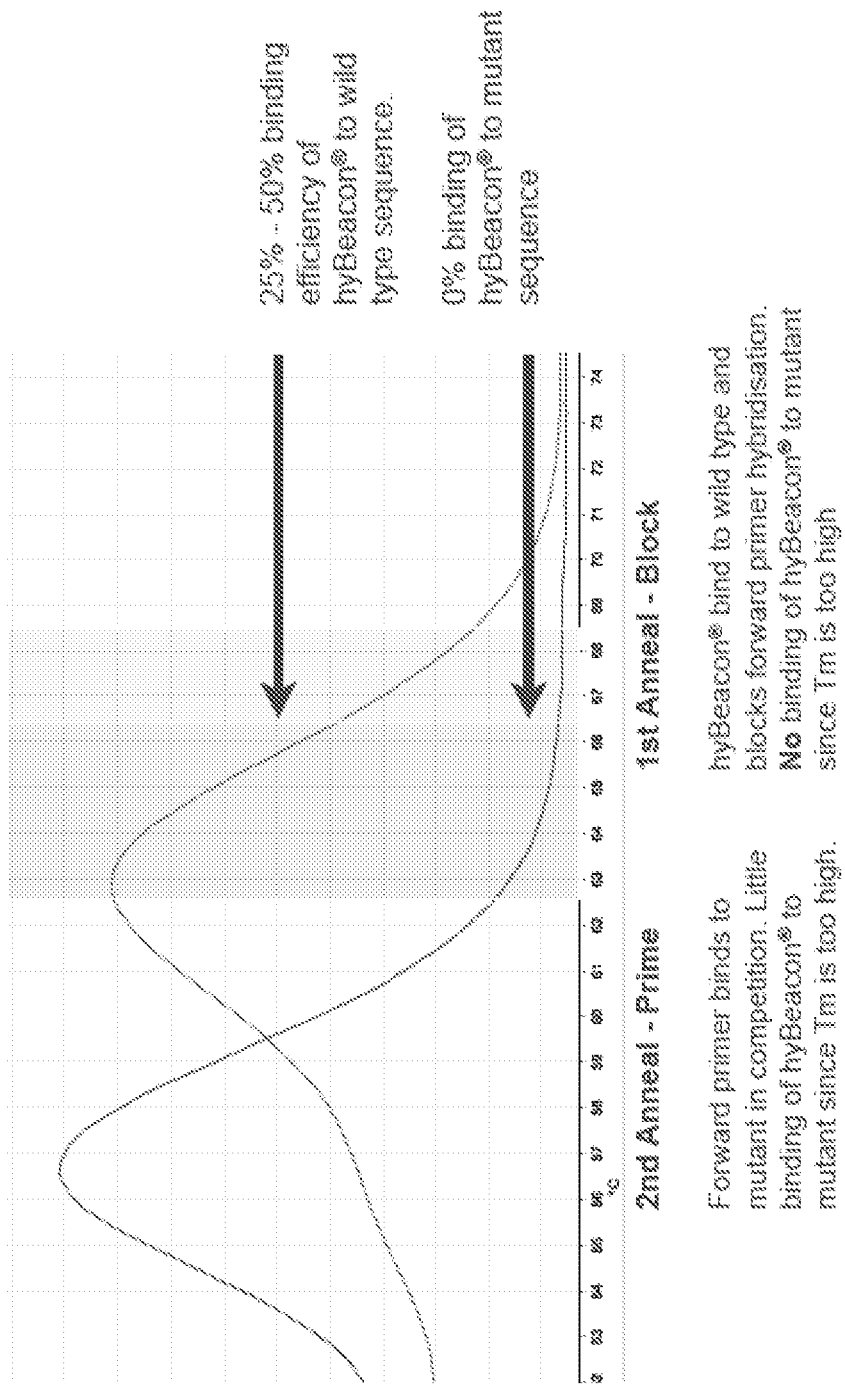

FIG. 20 depicts melting curve analysis to demonstrate an exemplary method for performing asymmetric amplification of a target sequence using blocking and Tm optimization methods as described in the invention.

Figure 21:
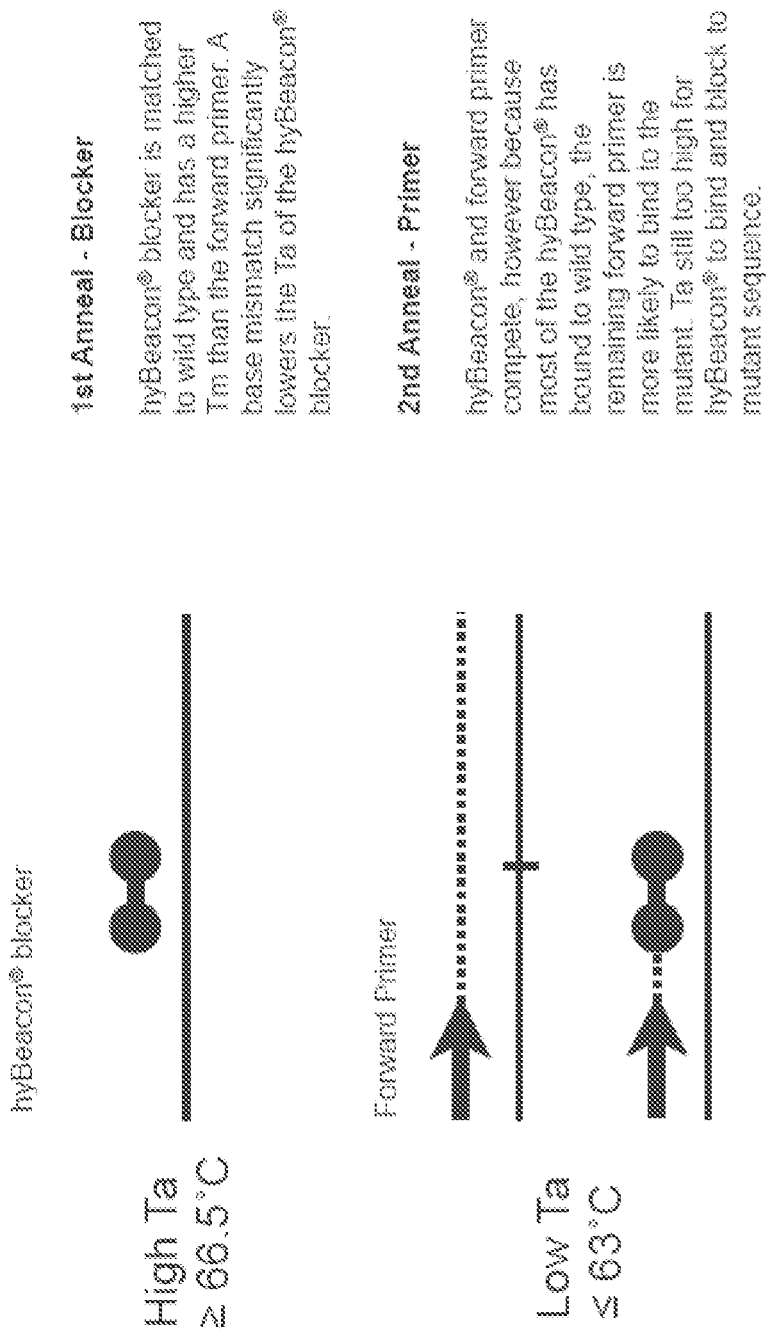
Figure 22:
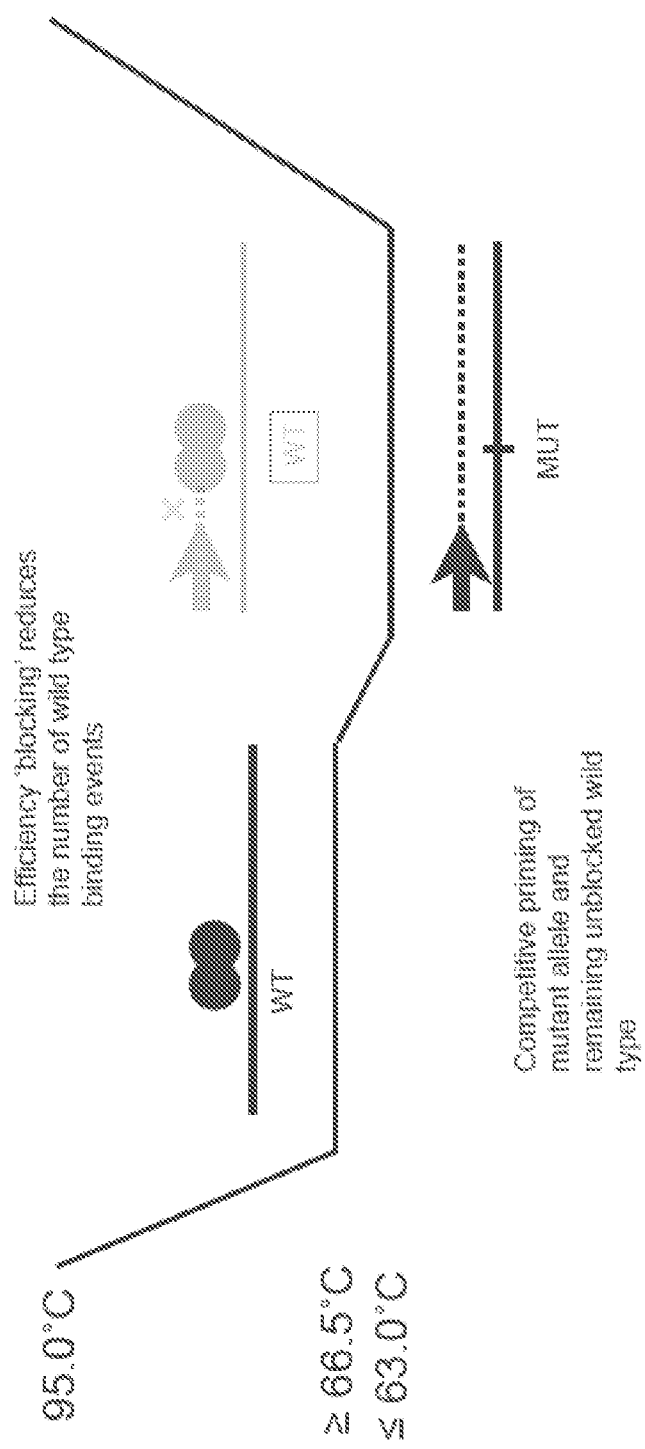
Figure 23:
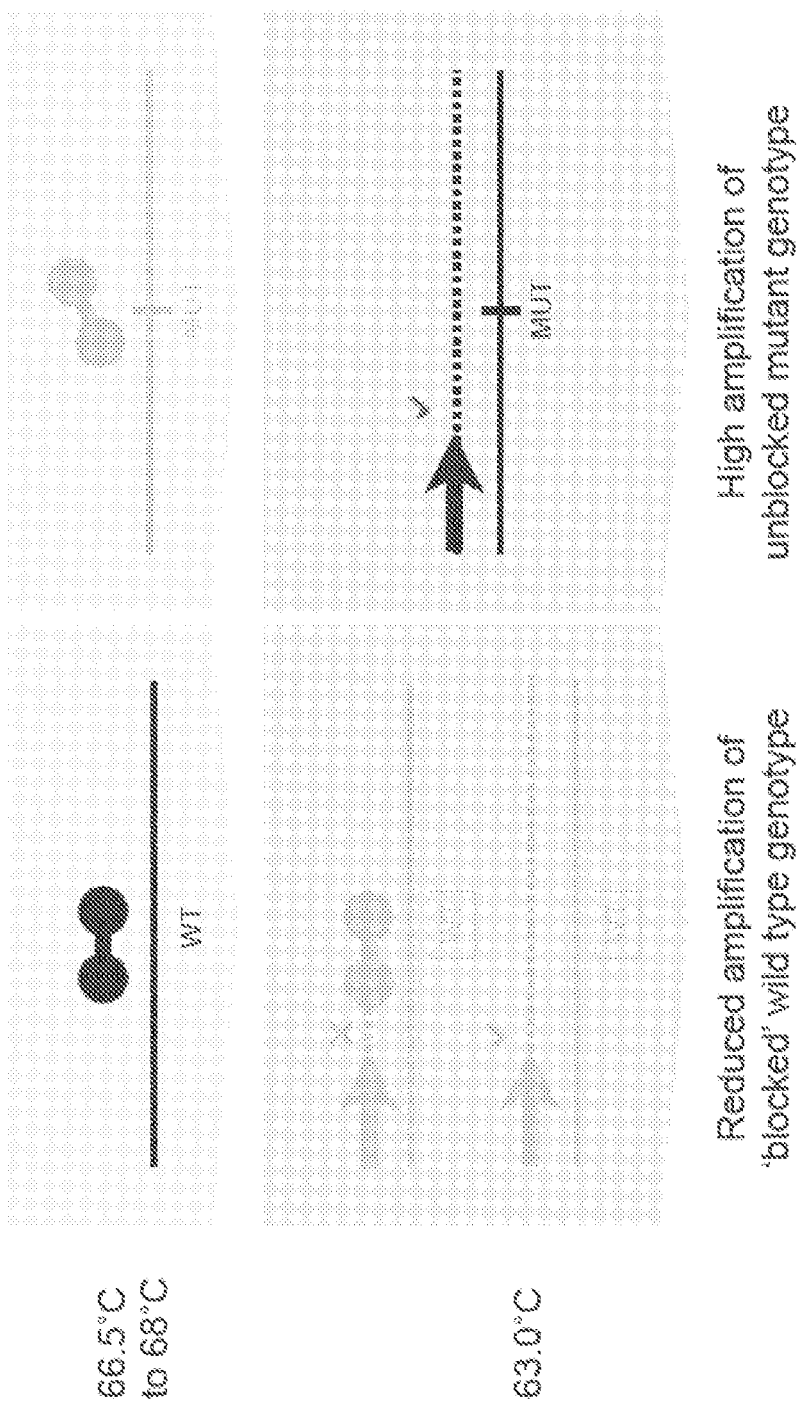

FIGS. 21-23 illustrates the various stages involved in an exemplary method for performing asymmetric amplification of a target sequence using blocking and Tm optimization methods as described in the invention.

DETAILED DESCRIPTION OF CERTAIN EMBODIMENTS

The present invention provides a method whereby low copy number mutations (for example, somatic mutations) may be preferentially amplified and detected, using a single probe as both a blocker, to prevent amplification of the unwanted allele, and a reporter, to report the presence of the mutant allele. Further, the probe can be used to detect multiple different alleles (for example, alternate SNPs) in the same locus from a single experiment. The method can be used to detect mutations such as SNPs as well as insertions or deletions.

We describe herein a number of examples showing the applicability of the method to different gene loci; however, it is clear that the method is of more general applicability.

There is a requirement to define clinical samples in order to orientate targeted therapies, for example for the purposes of personalised medicine. This requires rapid and reliable screening of somatic mutations. We show here that the method can be applied to three key somatic mutations in the genes K-RAS, EGFR and BRAF. The method as presented here makes use of hyBeacon® probes (which provide differential reporter signals depending on whether the probe is single stranded or double stranded) and asymmetric PCR (to preferentially amplify one strand of the target sequence). Typical sensitivity of the method is 1-5 copies of the mutant allele, and ratios greater than 5% SNP to wild type. A single assay using a single primer set and probe can detect multiple SNPs within the same probe sequence e.g. a single probe HYB_KRAS_CD12/13 detects all 12 mutations in K-RAS codon 12 and 13.

Example 1

K-RAS

A partial sequence of the wild type K-RAS gene is given in FIG. 1. Target regions in codons 12/13, 16, and 146 are highlighted in bold.

Figure 2:
FIG. 2 depicts a wild type sequence from K-RAS (WT_KRAS_CD12/12—SEQ ID NO. 10) as well as various SNPs within codons 12 and 13 of K-RAS, and their resulting amino acid substitution: KRAS_Gly12Ser—SEQ ID NO. 11; KRAS_Gly12Arg—SEQ ID NO. 12; KRAS_Gly12Cys—SEQ ID NO. 13; KRAS_Gly12Asp—SEQ ID NO. 14; KRAS_Gly12Ala—SEQ ID NO. 15; KRAS_Gly12Val—SEQ ID NO. 16; KRAS_Gly13Ser—SEQ ID NO. 17; KRAS_Gly13Arg—SEQ ID NO. 18; KRAS_Gly13Cys—SEQ ID NO. 19; KRAS_Gly13Asp—SEQ ID NO. 19; KRAS_Gly13Ala—SEQ ID NO. 20; KRAS_Gly13Val—SEQ ID NO. 21. Also depicted is an exemplary probe (HYB-B_KRAS_CD12/13—SEQ ID NO. 1) used to detect each of the SNPs identified in FIG. 2.

Codons 12 and 13 of K-RAS are susceptible to a large number of SNPs, resulting in the mutations Gly12 and/or Gly13 to Ser, Arg, Cys, Asp, Ala, Val. These possible mutations, and the corresponding DNA sequences, are shown in FIG. 2. Also shown in FIG. 2 is the sequence of the probe used to detect each of these SNPs, HYB_KRAS_CD12/13. As is apparent, the probe sequence is fully complementary to the relevant wild type target sequence, and has one mismatched base compared with each of the possible mutant sequences. The mismatch is internal to the probe, rather than at either of the ends. The probe is a hyBeacon® probe, having a pair of fluorophores which alter their emissions when the probe is in a double stranded duplex compared with single stranded form. The location of the fluorophores is marked.

FIG. 3 gives probe, wild type, and mutant sequences for the region around codons 61 (KRAS_GIn61Leu mutation; HYB_KRAS_CD61 probe) and 146 (KRAS_Ala146Thr mutation; HYB_KRAS_CD146 probe). In these examples there is only a single mutant allele, and a single mismatched base. Again, hyBeacon® probes were used.

Figure 4:
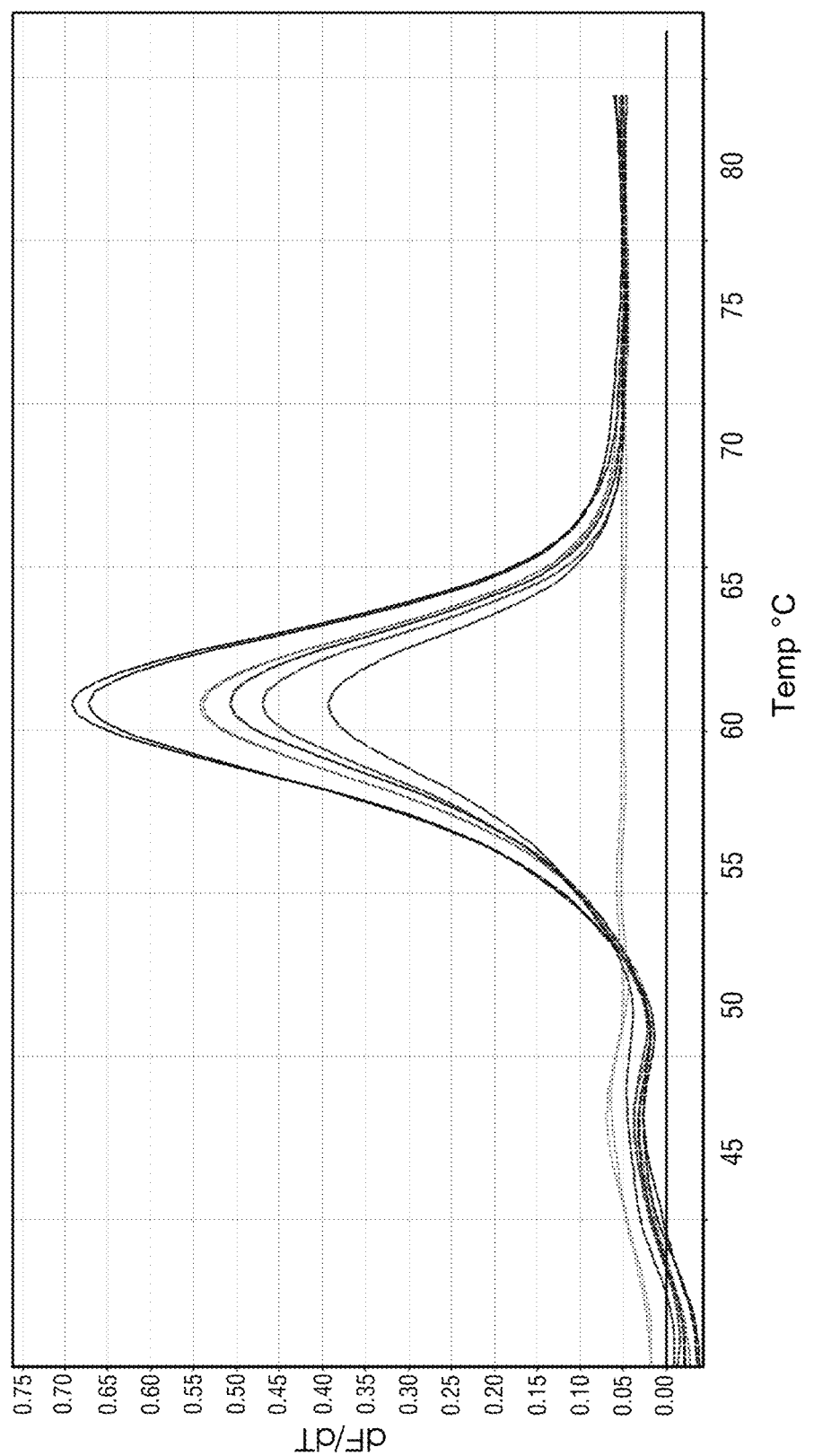
FIG. 4 presents data demonstrating the melt curve for the HYB_KRAS_CD12/13 probe versus wild type DNA.
Figure 6B:
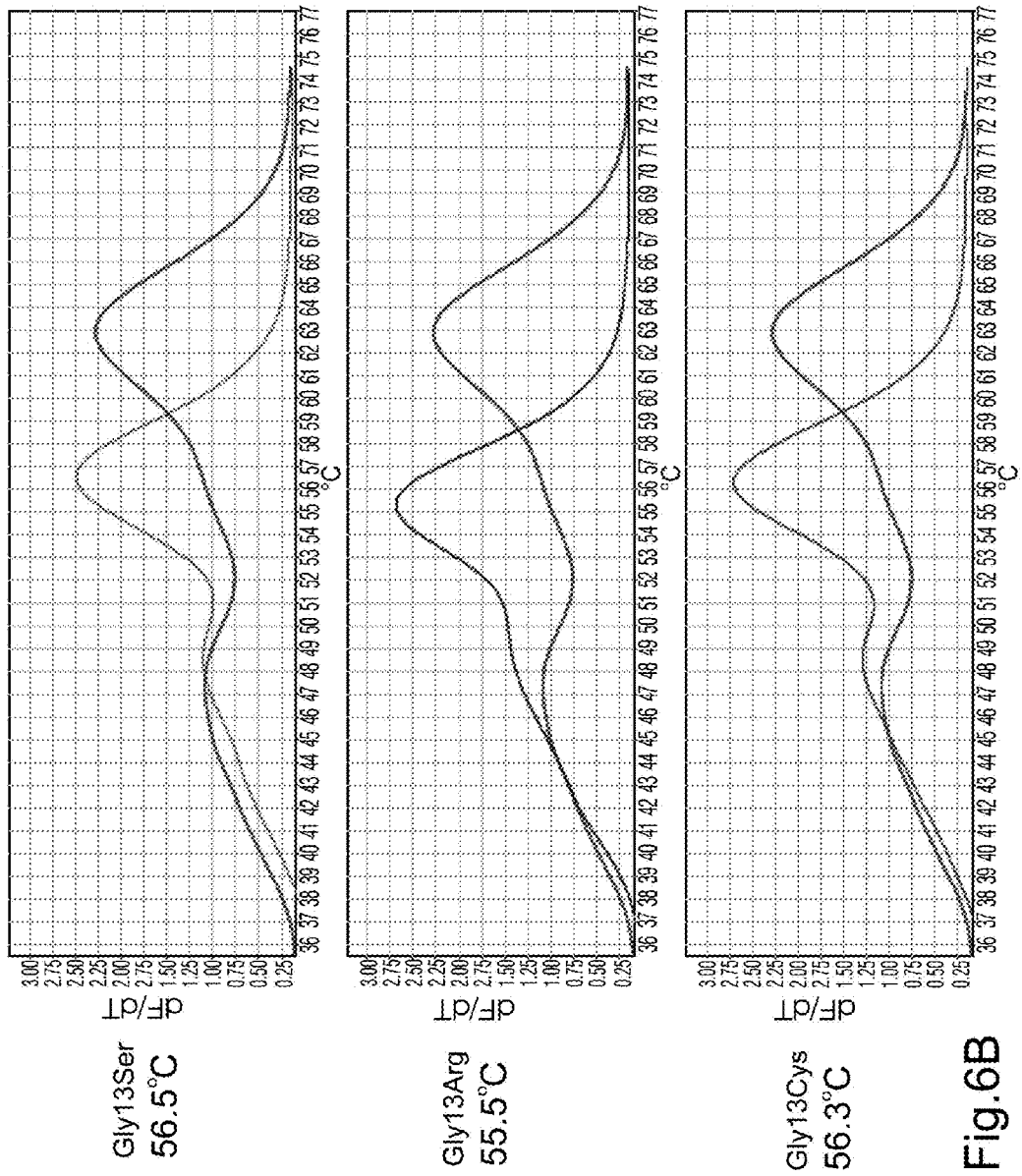
Figure 6C:
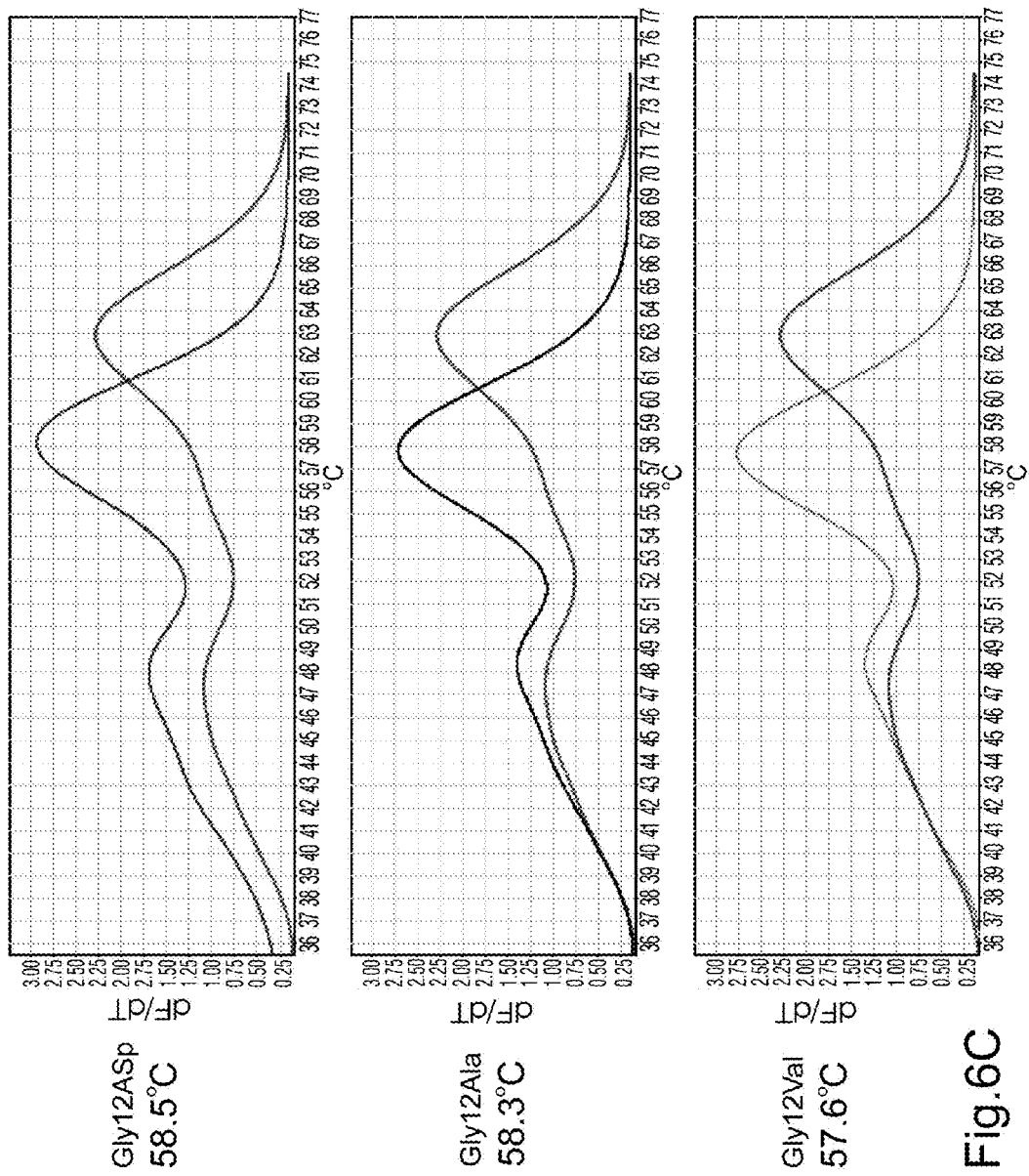
Figure 6D:
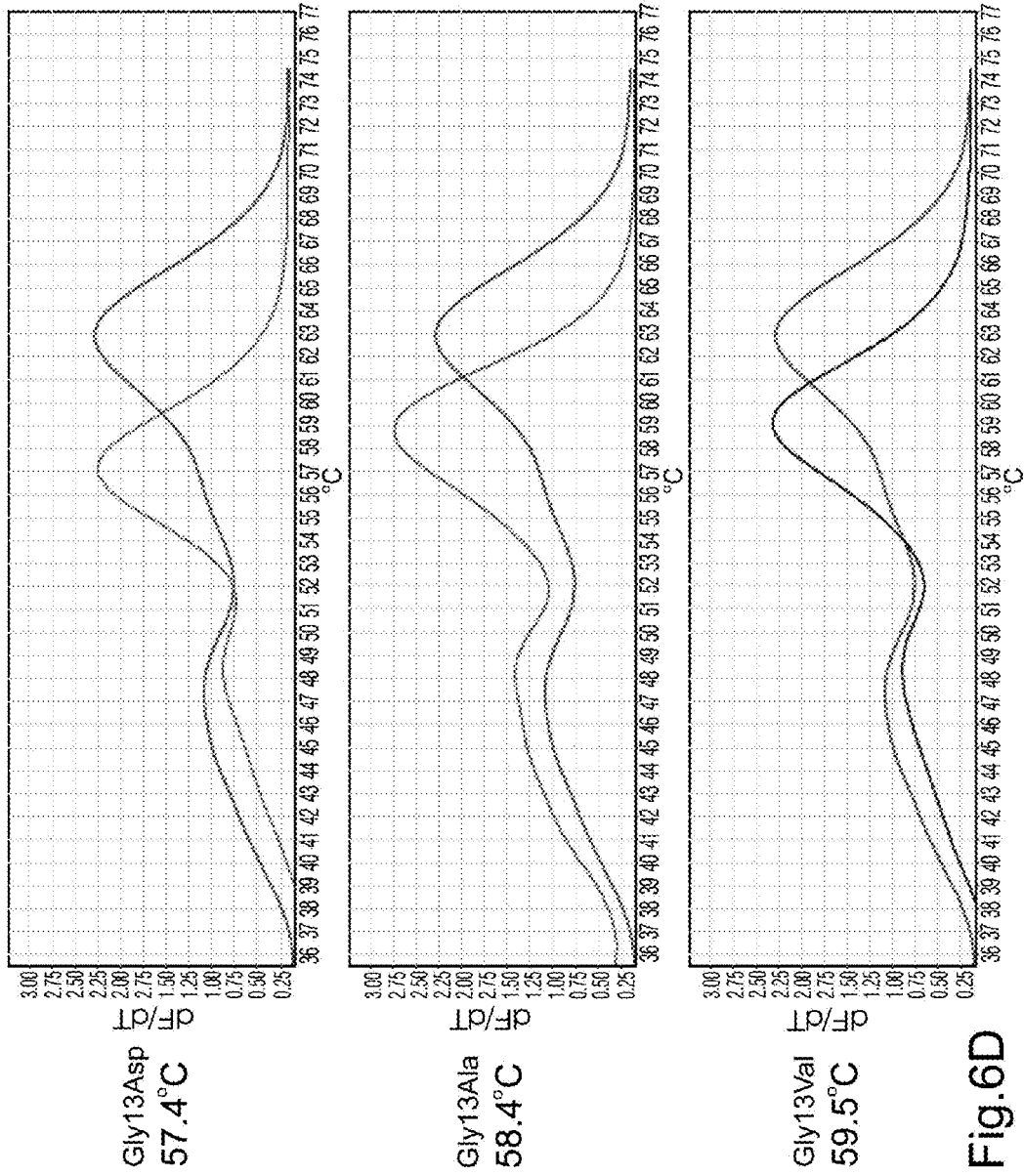

FIG. 4 shows the melt curve for the HYB_KRAS_CD12/13 probe versus wild type DNA. FIG. 5 shows a table indicating the Tm for the CD12/13 probe hybridised to each of the wild type and mutant alleles. It will be noted that each Tm is clearly distinguishable from at least the majority of the other Tms, and in particular within a tolerance of 0.1 deg C. the only potential duplicate is Gly12Ser and Gly13Ser, with Tm of 56.7 and 56.5 deg C. respectively. FIG. 6 gives melt curves for each of the CD12/13 alleles compared with the wild type melt curve. These experiments show that the HYB_KRAS_CD12/13 probe can be used to distinguish between each of the possible alleles in codons 12 and 13.

Figure 7:
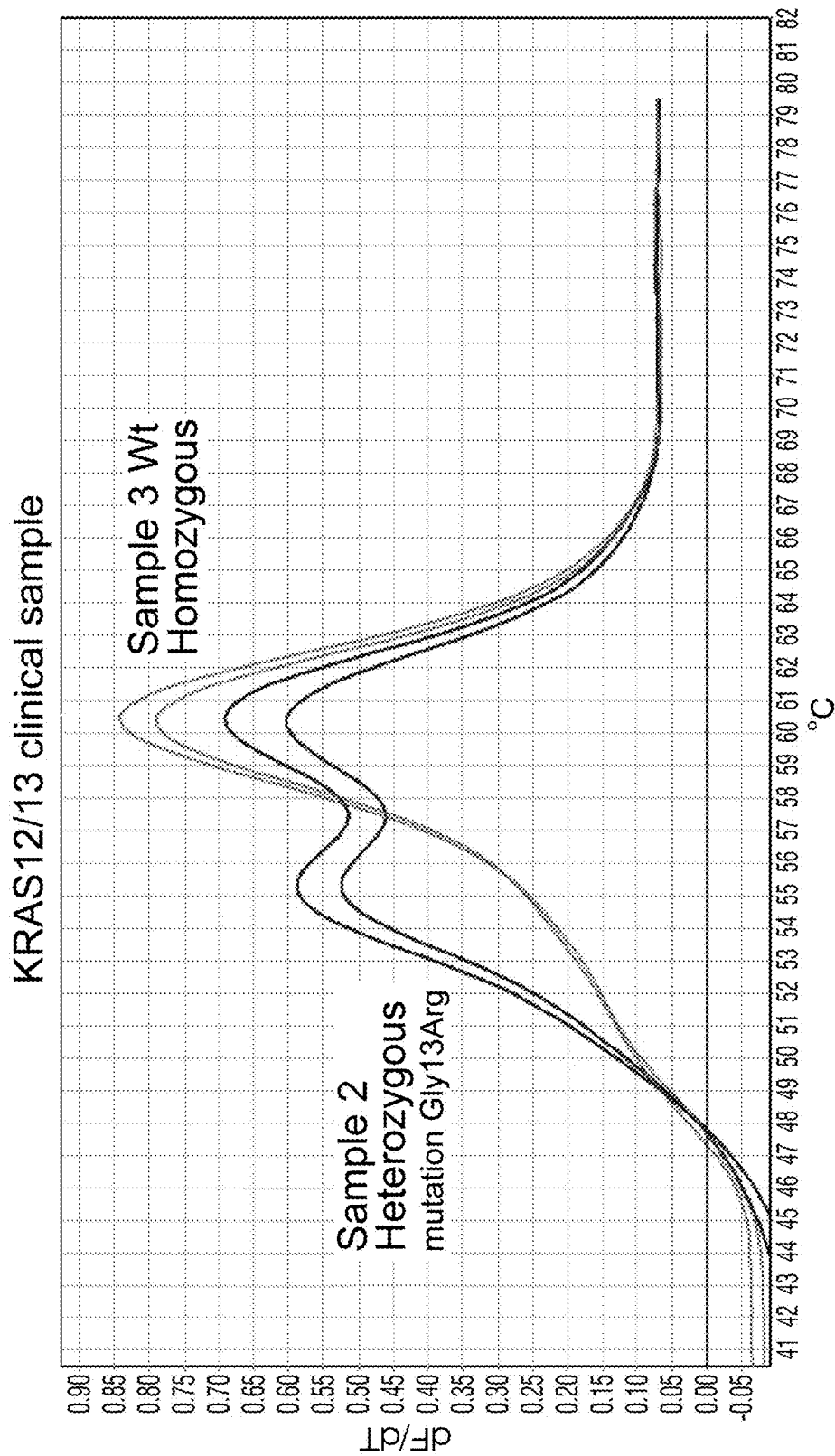
FIG. 7 depicts the melt curve for two clinical samples tested using the HYB_KRAS_CD12/13 probe. Sample 2 is heterozygous for the wild type allele and the Gly13Arg allele. Sample 3 is homozygous for the wild type allele.

FIG. 7 gives melt curves comparing two samples—one wild type homozygous, and one Gly13Arg/wild type heterozygote. The heterozygote can be clearly distinguished from the homozygote, and the temperature of the Gly13Arg peak is consistent with that shown in FIG. 6.

Figure 8:
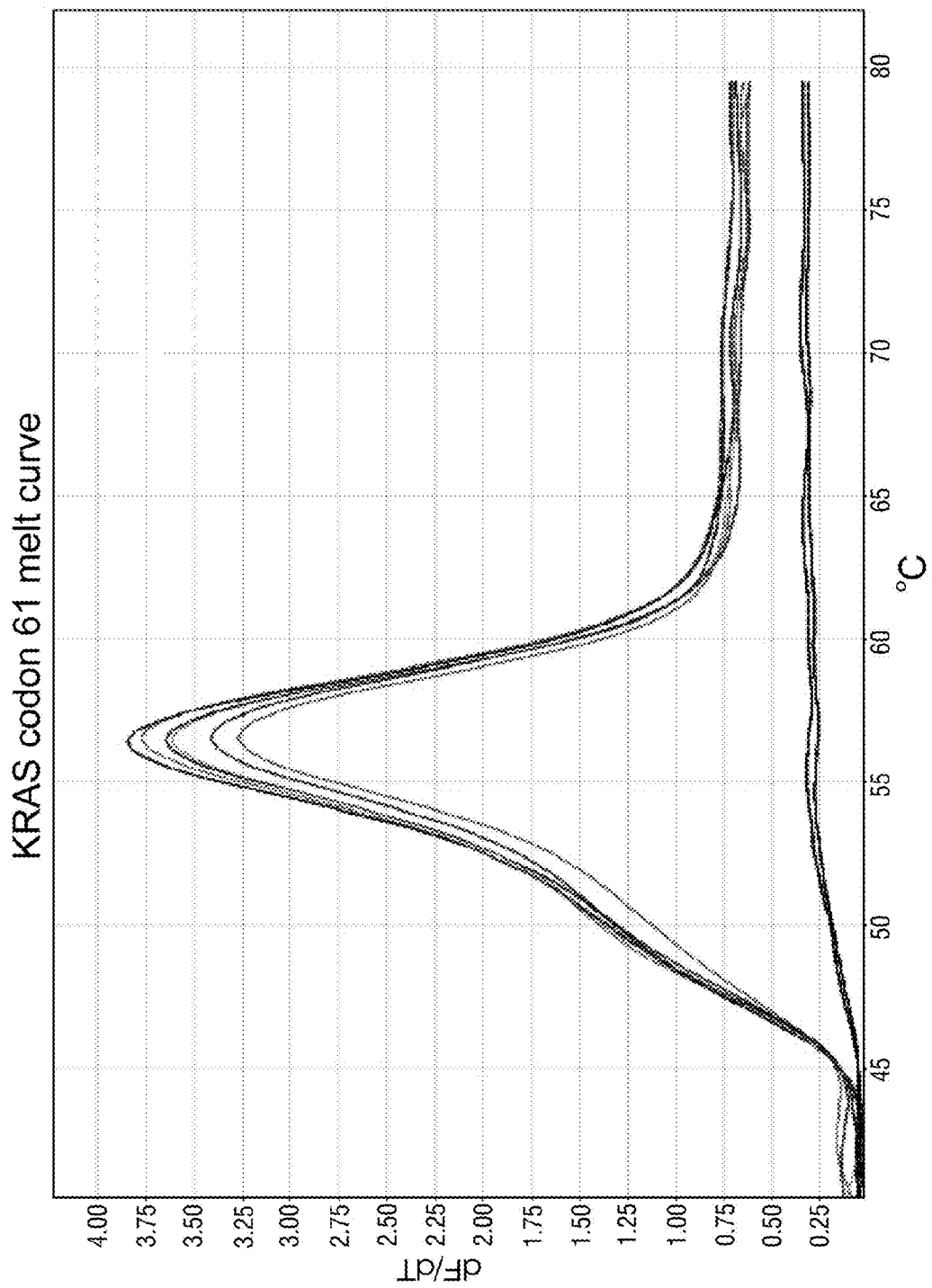
FIG. 8 depicts the melt curve for codon 61 mutant allele using the HYB_KRAS_CD61 probe.
Figure 9:
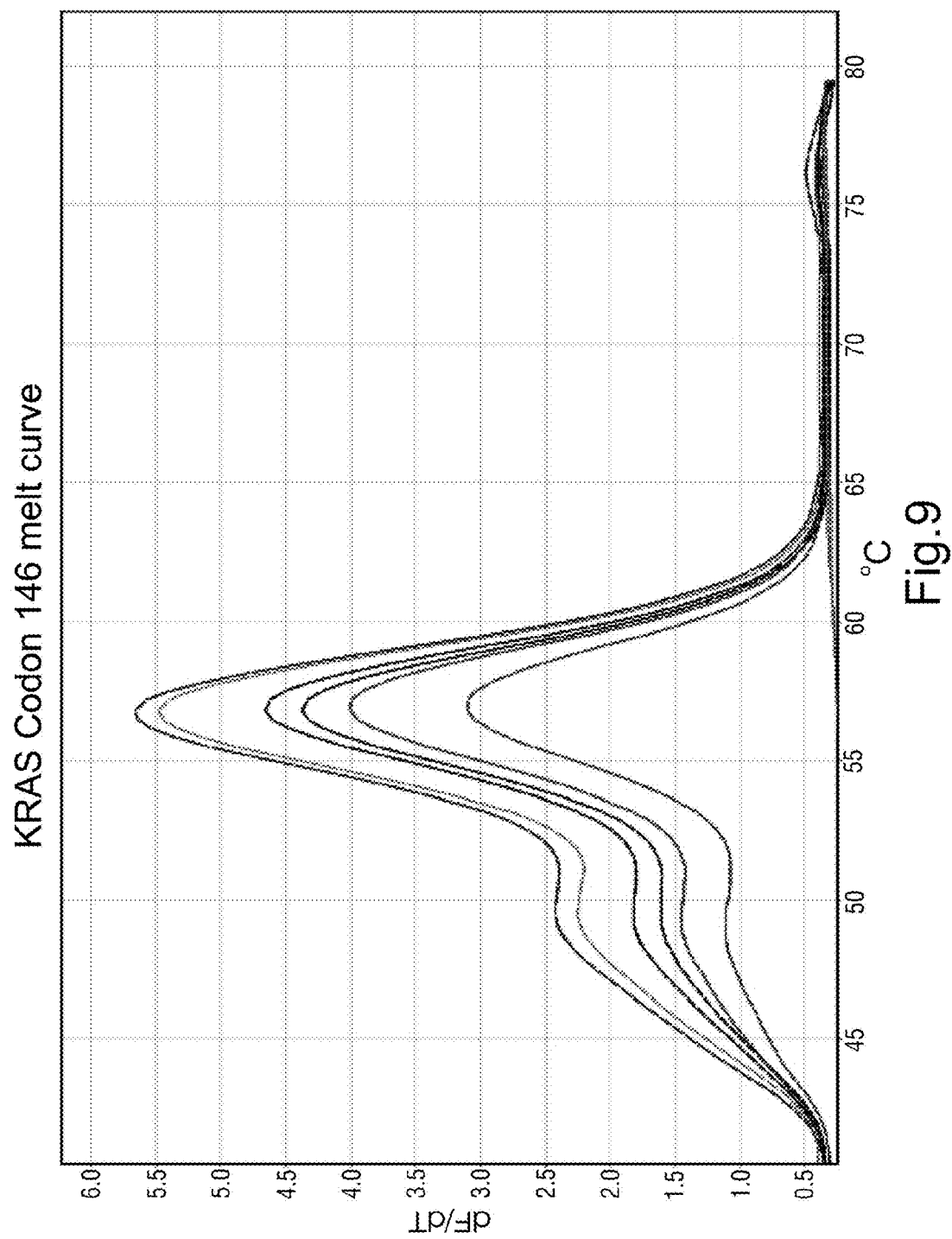
FIG. 9 depicts the melt curve for codon 146 mutant allele using the HYB_KRAS_CD146 probe.

FIGS. 8 and 9 show melt curves for the KRAS codon 61 and 146 mutants respectively.

Together, these experiments confirm assay sensitivity down to single copy (1-5 copies). The melt curves provide analysis of mutations in codons 12, 13, 61 and 146. All 12 mutations in codon 12 and 13 are identifiable from wild type and from each other.

Example 2

EGFR

Figure 10:
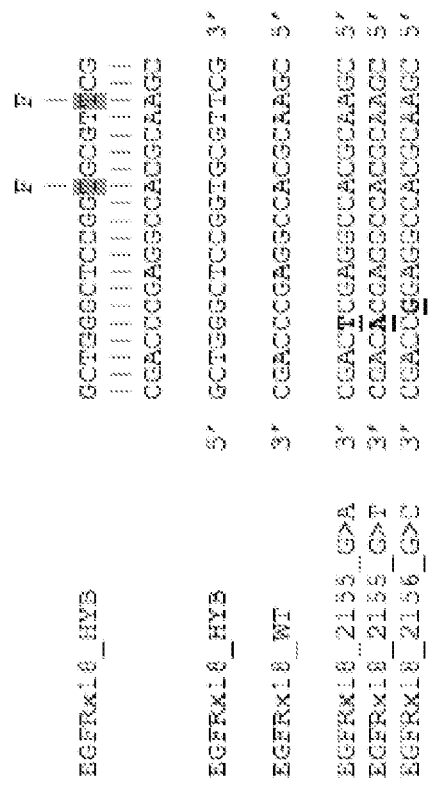
FIG. 10 depicts a wild type sequence from EGFR (EGFRx18_WT—SEQ ID NO. 27) as well as various SNPs within exon18 of the EGFR gene (EGFRx18_2155_G>A—SEQ ID NO. 28; EGFRx18 2155 G>T—SEQ ID NO. 29; EGFRx18 2155 G>C—SEQ ID NO. 30), along with their corresponding nucleic acid substitutions. Also depicted is an exemplary probe (EGFRx18_HYB—SEQ ID NO. 4) used to detect each of the SNPs identified in FIG. 10.

FIG. 10 shows the EGFR probe sequence (EGFRX18_HYB) for the EGFR exon 18 region. The probe sequence is fully complementary to the wild type region, while there are three potential SNP mutations (2155 G>A, 2155 G>T, and 2156 G>C), each of which differs from the probe sequence by a single mismatched base. Again, the EGFRX18_HYB probe is a hyBeacon® probe having two fluorescent moieties.

Figure 12:
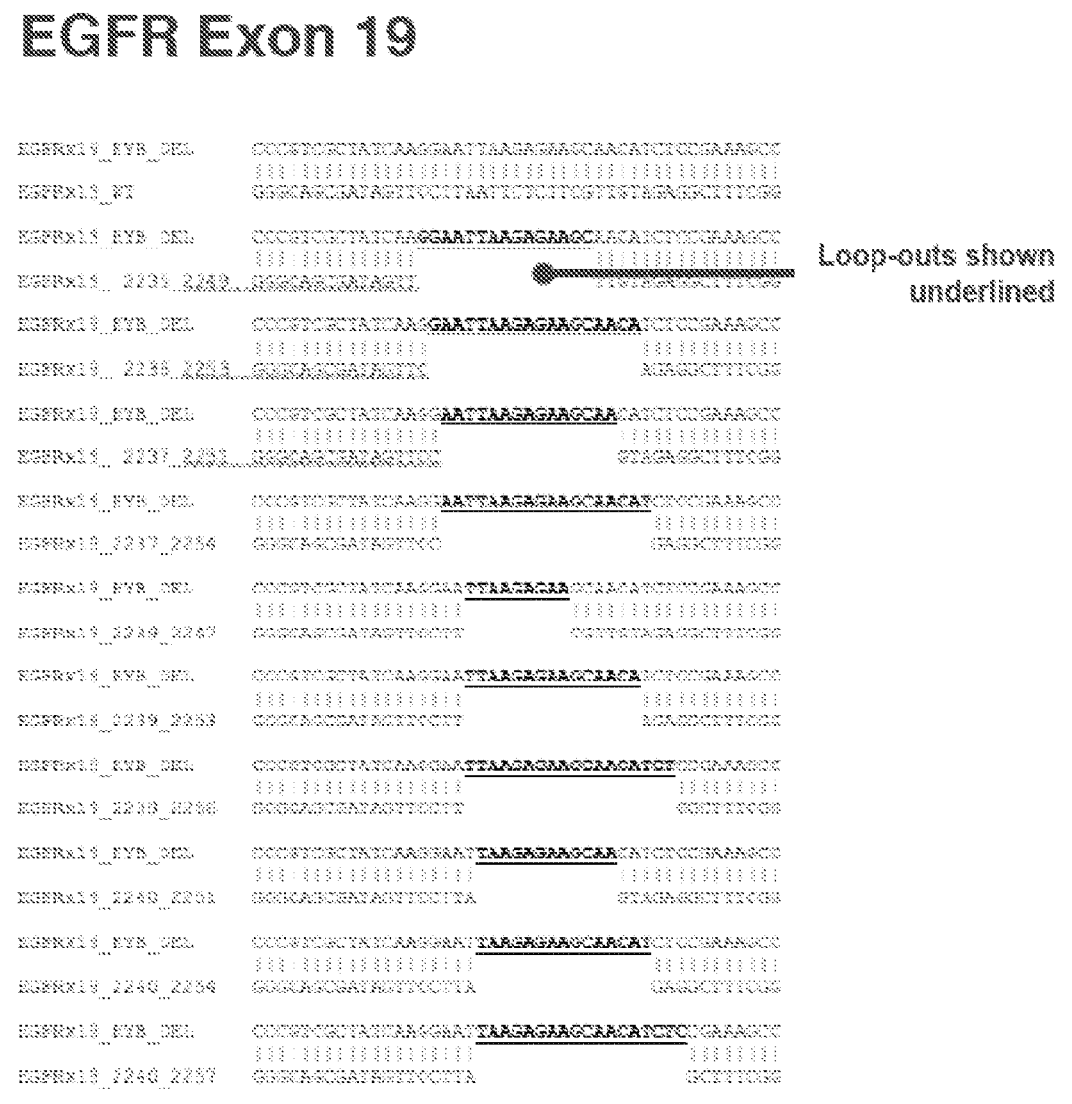

FIG. 11 shows an EGFR probe sequence (EGFRX19_HYB) for EGFR exon 19. Unlike exon 18, in which the mutant form is a SNP, exon 19 may carry various deletion mutants. The potentially deleted region is shown in bold in FIG. 11, while FIG. 12 shows the exon 19 probe hybridised to a number of deletion mutants of varying lengths. The underlined regions of the probe do not hybridise to the target, and so form a loop. This alters the Tm of the probe:target duplex, in much the same way as the presence of a base mismatch in a SNP. The change in Tm depends on the size of the unhybridised region, and so this probe can be used to identify specific mutants.

Figure 13:
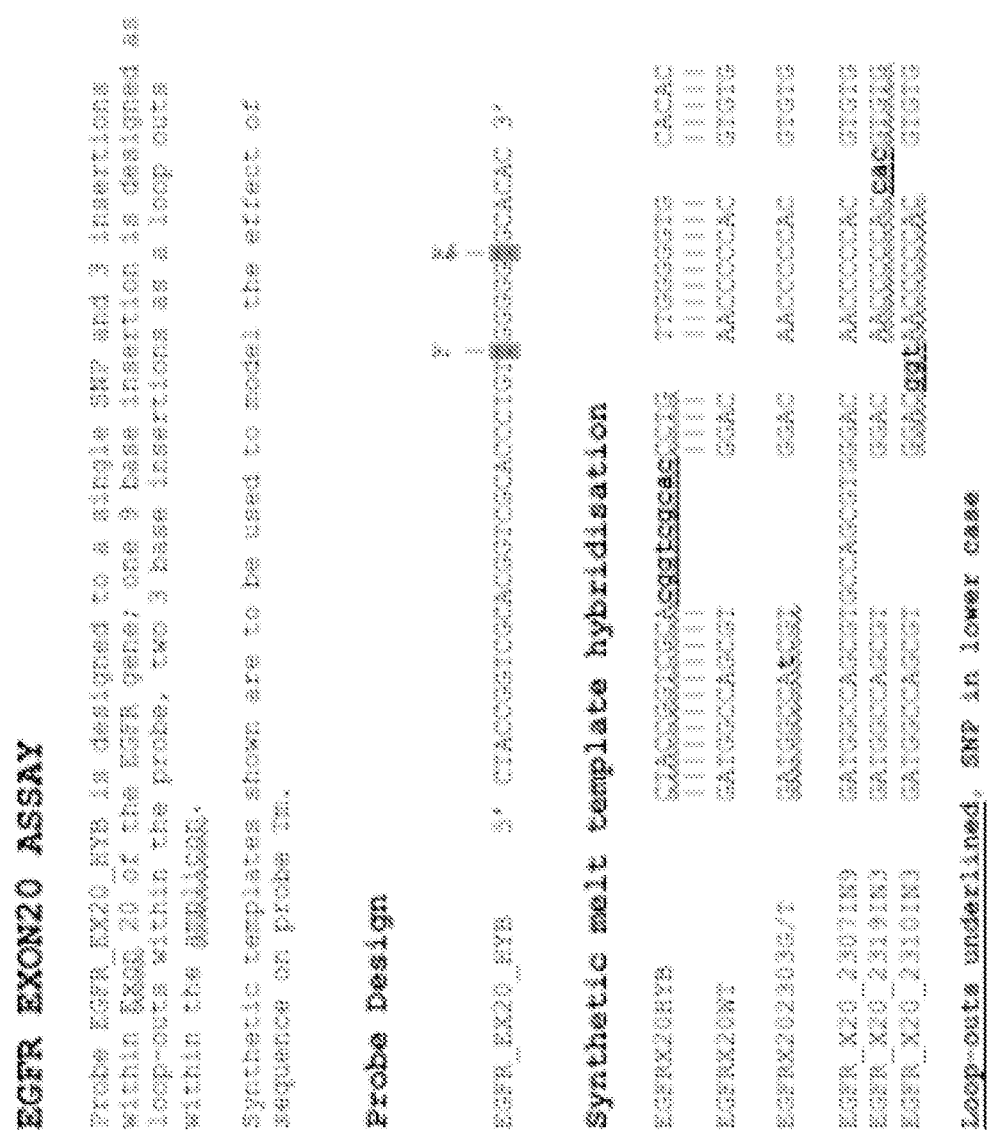

FIG. 13 shows another EGFR probe sequence, this time designed to detect insertion and SNP mutants in exon 20. The SNP is 2303 G>T, while there are three possible insertions, a 9 by insertion at base 2307, and two 3 by insertions at bases 2310 and 2319. The probe is designed with a fully complementary sequence to the 9 by insertion mutant; there is thus a 9 by loop formed in the probe when hybridising to the other mutants, and a 3 by loop formed in the target when hybridising to either of the 3 by insertion mutants. Hybridisation to the SNP mutant gives a single base mismatch as well as the 9 by probe loop. This arrangement was chosen with the intention of providing clearly distinguishable Tm for each potential hybridisation.

Figure 14:
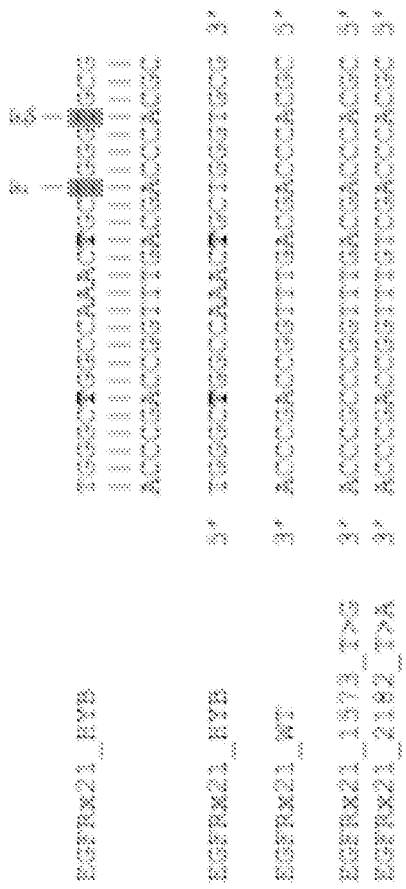
FIG. 14 depicts the EGFR_EX21_HYB probe (SEQ ID NO. 7), a wild type sequence (EGFRx21WT—SEQ ID NO.

FIG. 14 shows an EGFR probe sequence EGFRX21_HYB designed to detect two SNPs in exon 21, 1573 T>G and 2182 T>A.

FIG. 15 shows a melt curve from samples tested with the EGFRX19_HYB probe. Sample A is an insertion mutant, and shows a distinct peak at 59 deg C., while sample B is wild type, and shows only the wild type peak at 73 deg C. This wild type peak is also seen in sample A. Genomic wild type DNA included as a control also shows the 73 deg C. peak.

A melt curve from samples tested with the EGFRX20_HYB probe is shown in FIG. 16. All samples were wild type, and show a peak at around 66.8 deg C.

Example

BRAF

The BRAF gene includes several potential SNP mutations in amino acid 600: 1799 T>A, G, or C, as well as multiple mutations, 1799 TG>AT, 1798 GT>AA or AG, and 1797 AGT>GAG. The hyBeacon® probe BRAFV600_HYB is fully complementary to a portion of the wild type sequence. The probe and the various target sequences are shown in FIG. 17.

FIG. 18 shows the location of primer sequences used to amplify the BRAFV600 region; these are outside the probe region. Primer targets are underlined, and the probe target is in bold. The figure shows the genomic sequence; the probe will be complementary, as will one of the primers.

These primers were used to amplify a number of samples, and to monitor hybridisation of the probe to the amplified sequence using real-time PCR. The melt curve is shown in FIG. 19. The main peaks for all samples are at around 52 deg C., representing the wild type sequence. Mutant sequences cluster with peaks around 44 deg C. Some samples show peaks at both temperatures, representing heterozygous samples.

Example

Preferential Amplification of Mutant Genotypes

Due to the small percentage of somatic mutation within any given sample against a background of wild type sequence, a systematic approach to assay design is usually necessary to improve the performance and sensitivity of mutation detection. Generally knowledge of the mutation is required to target amplification from specific mutation sites, and multiple primers are required for multiple mutations. However, the methods disclosed herein avoid the need for such knowledge. As well as somatic mutations, the methods may find other applications; for example, low-abundance HIV drug-resistant variants can increase a subject's overall burden of resistance, yet commonly go unrecognised by conventional genotyping.

The amplification methods described herein use asymmetric PCR, which preferentially amplifies one strand of the target DNA. Standard thermal cycling is carried out as in conventional PCR, but with a limiting amount of one primer (rate limited primer). When the limiting primer becomes depleted, replication increases arithmetically through extension of the excess primer.

Typically the probe is complementary to the non-primer-limited strand, so that the preferentially amplified strand may hybridise to the probe. The probe may then block amplification of that strand if hybridisation takes place—for example, if the sequence is that of the wild type rather than the mutant.

The skilled person will be able to design suitable primers for use in the present method, to amplify a desired target sequence.

The probes used have a significantly higher melt temperature (Tm) when binding to the wild type than to the mutant. This allows use of the probe both as a blocker, to prevent amplification, and as a reporter, to report on the presence of the wild type or mutant sequence.

Using a hold/extension temperature set above the Tm of the probe:wild type duplex it is possible to preferentially bind the probe to the wild type without significant hybridisation to the mutant sequence. The anneal of the amplification primers is also chosen to be above the Tm of the probe: mutant duplex. The amplification primers bind to both wild type and mutant alleles, but amplification of the wild type is significantly reduced because of the blocking probe. This preferentially increases the population of mutant for subsequent rounds of amplification.

A melt curve to illustrate the process is shown in FIG. 20. The first annealing step is at a high temperature (in this case, 66.5 deg C.). In this blocking step, the probe binds to wild type and blocks forward primer hybridisation. There is no binding of the probe to the mutant, since Tm is too high. In the second annealing step, at a lower temperature (here, 57 deg C.) the forward primer binds to the mutant in competition. There is little binding of the probe to the mutant since Tm is too high.

The amplification method is shown in more detail in FIGS. 21-23. In the first anneal (blocking) stage (FIG. 21), carried out at a high temperature (eg, 66.5 deg C.) the probe blocker is matched to wild type and has a higher Tm than the forward primer. A base mismatch significantly lowers the Tm of the blocker. In the second anneal (primer) stage (FIG. 21), carried out at a low temperature (eg, 63 deg C.), the probe and forward primer compete, however because most of the probe has bound to wild type, the remaining forward primer is more likely to bind to the mutant. The temperature is still too high for the probe to bind and block to mutant sequence.

FIG. 22 shows the temperature through a single cycle of the amplification reaction. The melt phase takes place at 95 deg C., then the temperature is lowered to 66.5 deg C. for the blocking anneal phase. It is then lowered further to 63 deg C. for the primer anneal and extension phases, before cycling back to 95 deg C. As shown in FIG. 23, the mutant sequence is amplified, while the wild type is blocked. There may still be some amplification of the wild type sequence, but the mutant sequence is preferentially amplified, so increasing relative abundance in the sample.

Once the sample is amplified, the type of mutant sequence may be determined by carrying out the melt curve analysis described above with respect to KRAS, EGFR, or BRAF. A benefit of using the hyBeacon® probes, or similar, is that the same single probe both blocks amplification of wild type to enrich amplification of mutant sequence, and reports both wild type:mutant ratio at the end of the assay. The method allows amplification of any mutant sequences within the probe region, and is completely independent of any SNP knowledge; i.e. can report unknown SNPs within the probe sequence. A single probe can enrich mutant SNPs on multiple codons within the single probe, and or multiple probes along a stretch. The technique can also be used to detect insertions/deletions, and is compatible with asymmetric amplification.

The invention claimed is:

1. A method of preferentially amplifying and detecting a first allele of a locus having at least first and second alleles, the method comprising:
   a) providing a reaction mix comprising
      i) a sample including nucleic acid representing at least the locus to be amplified;
      ii) an oligonucleotide probe which hybridises to the first allele with a lower melting temperature (Tm) than that with which it hybridises to the second allele;
      iii) a pair of oligonucleotide primers for nucleic acid amplification, the primers hybridising to the nucleic acid in the sample at first and second sites flanking the oligonucleotide probe binding site; wherein the Tm of the primer:sample is higher than the Tm of the probe: first allele;
   b) maintaining the reaction mix at a temperature between the probe:first allele Tm and the probe:second allele Tm, such that the probe preferentially hybridises to the second allele;
   c) carrying out a thermal cycling amplification on the reaction mix, the amplification including a melt phase, an annealing phase, and an extension phase, in which the temperatures of the extension and annealing phases are between the probe:first allele Tm and the probe:second allele Tm, such that the probe is hybridised to the second allele during these phases; to thereby amplify the first allele; and
   d) detecting hybridisation of the probe to the sample at a temperature at or below the probe:first allele Tm; detecting hybridisation of the probe to the sample at a higher temperature at or below the probe:second allele Tm; and comparing the two; to thereby detect the amplified first allele;
   wherein the probe is labelled with a fluorescent label which generates a differential signal depending on whether the probe has hybridised to a target strand;
   wherein one of the primers is provided in a rate-limiting amount, and the amplification reaction is asymmetric PCR; and
   wherein one or both of the primers overlap with the probe binding site such that the probe competes with the primer for binding, to thereby prevent binding of the primer and hence strand extension.

2. The method of claim 1 wherein the first allele is a mutant allele and the second allele is a wild type allele.

3. The method of claim 1 wherein the temperature of the melt phase is higher than the temperatures of the Tm primer : sample and the Tm probe : second allele.

4. The method of claim 1 wherein the locus is a multi-allelic locus; that is, there is a wild type allele and more than two mutant alleles possible at that locus.

5. The method of claim 4 wherein the probe is selected such that the Tm probe:wild type allele is lower than any of the Tm probe : mutant alleles.

6. The method of claim 4 wherein the Tm of each possible probe:allele combination differs.

7. The method of claim 6 wherein the Tm of each combination differs by at least 0.1 C. degree, preferably at least 0.25 C. degree, more preferably at least 0.5 C. degree, most preferably at least 0.75 C. degree.

8. The method of claim 1 wherein the probe is fully complementary to one strand of the second allele.

9. The method of claim 1 wherein the first allele differs from the sequence of the second allele by one or more point mutations.

10. The method of claim 1 wherein the first allele differs from the sequence of the second allele by a plurality of single nucleotide polymorphisms (SNPs).

11. The method of claim 1 wherein the first allele differs from the sequence of the second allele by one or more deletions and/or insertions.

12. The method of claim 1 wherein the probe is DNA.

13. The method of claim 1 wherein the differences in sequence between the first and second alleles are internal to the region where the probe binds.

14. The method of claim 1 wherein the locus is multi-allelic, and the detection step further comprises raising the reaction mix to one or more intermediate temperatures, and detecting hybridised probe molecules at each intermediate temperature.

15. The method of claim 1 wherein a first primer binds 3'-wards of the probe target, while a second primer binds 5'-wards of the probe target.

16. The method of claim 1 wherein the target locus is selected from the KRAS, EGFR, or BRAF human genes.

17. The method of claim 1 wherein the target loci are selected from codons 12 and 13 of KRAS, codon 61 of KRAS, and codon 146 of KRAS.

18. The method of claim 1 wherein the target loci are selected from exons 18, 19, 20, or 21 of EGFR.

19. The method of claim 1 wherein the target locus is amino acid residue 600 of BRAF, and corresponding nucleotide residues.

20. The method of claim 1 wherein the probe sequence is selected from the group consisting of:

5' AGTTGGAGCTGGTGGCGTAG 3' (HYB_KRAS_CD12/13, SEQ ID NO 1), targeting codons 12 and 13 of KRAS 5' AGGTCAAGAGGAGTACAGTG 3' (HYB_KRAS_CD61, SEQ ID NO 2), targeting codon 61 of KRAS 5' TGTAGTCGTTTCTGTTCTGT 3' (HYB_KRAS_CD146, SEQ ID NO 3), targeting codon 146 of KRAS 5' GCTGGGCTCCGGTGCGTTCG 3' (EGFRX18_HYB, SEQ ID NO 4), targeting exon 18 of EGFR 5' CCCGTCGCTATCAAGGAATTAAGAGAAGCAACATCTCCGAAAGCC 3' (EGFRX19HYB_DEL, SEQ ID NO 5), targeting exon 19 of EGFR 5' CTACCGGTCGCACGGTCGCACCCTGTTGGGGGTGCACAC 3' (EGFRX20_HYB, SEQ ID NO 6), targeting exon 20 of EGFR 5' TGGGCTGGCCAAACTGCTGGGTGCG 3' (EGFRX21_HYB, SEQ ID NO 7), targeting exon 21 of EGFR 5' CTACAGTGAAATCTCGATGG 3' (BRAF_V600, SEQ ID NO 8), targeting amino acid 600 of BRAF.

21. A method for detecting somatic mutations in a sample from a subject, the sample comprising nucleic acid from a locus having at least first and second alleles, the first allele being a mutant allele and the second allele being a wild type allele, the method comprising
   a) providing a reaction mix comprising
      i) the sample;
      ii) an oligonucleotide probe which hybridises to the first allele with a lower melting temperature (Tm) than that with which it hybridises to the second allele;
      iii) a pair of oligonucleotide primers for nucleic acid amplification, the primers hybridising to the nucleic acid in the sample at first and second sites flanking the oligonucleotide probe binding site; wherein the Tm of the primer:sample is higher than the Tm of the probe: first allele;
   b) maintaining the reaction mix at a temperature between the probe:first allele Tm and the probe:secod allele Tm, such that the probe preferentially hybridises to the second allele;
   c) carrying out a thermal cycling amplification on the reaction mix, the amplification including a melt phase, an annealing phase, and an extension phase, in which the temperatures of the extension and annealing phases are between the probe:first allele Tm and the probe:second allele Tm, such that the probe is hybridised to the second allele during these phases; to thereby amplify the first allele;
   d) maintaining the temperature of the reaction mix at or below the Tm probe:mutant allele;
   e) maintaining the temperature of the reaction mix above the temperature in step d), but at or below the Tm probe : wild type allele; and
   f) detecting hybridised probe in steps d) and e), to thereby determine the presence or absence of the mutant allele in the sample;
   wherein the probe is labelled with a fluorescent label which generates a differential signal depending on whether the probe has hybridised to a target strand;
   wherein one of the primers is provided in a rate-limiting amount, and the amplification reaction is asymmetric PCR; and
   wherein one or both of the primers overlap with the probe binding site such that the probe competes with the primer for binding, to thereby prevent binding of the primer and hence strand extension.

* * * * *